US010365196B2

(12) United States Patent
Gimenez Calbo et al.

(10) Patent No.: US 10,365,196 B2
(45) Date of Patent: Jul. 30, 2019

(54) WATER TENSION SENSOR, SYSTEM FOR CHARACTERISING AND CONTINUOUSLY MEASURING SOIL WATER, SYSTEM FOR INDICATING CRITICAL SOIL WATER TENSION AND IRRIGATION ROD

(71) Applicants: Empresa Brasileira de Pesquisa Agropecuaria—Embrapa, Brasília (BR); Tecnicer Tecnologia Ceramica LTDA, Sao Carlos (BR)

(72) Inventors: Adonai Gimenez Calbo, Sao Carlos (BR); Carlos Manoel Pedro Vaz, Sao Carlos (BR); Waldir Aparecido Marouelli, Brasilia (BR); Luis Fernando Porto, Sao Carlos (BR)

(73) Assignees: EMPRESA BRASILEIRA DE PESQUISA AGROPECUÁRIA—EMBRAPA, Brasília-DF (BR); TECNICER TECHNOLOGIA CERÂMICA LTDA, São Carlos-SP (BR)

( * ) Notice: Subject to any disclaimer, the term of this patent is extended or adjusted under 35 U.S.C. 154(b) by 672 days.

(21) Appl. No.: 14/786,480

(22) PCT Filed: Apr. 24, 2014

(86) PCT No.: PCT/BR2014/000128
§ 371 (c)(1),
(2) Date: Apr. 4, 2016

(87) PCT Pub. No.: WO2014/172765
PCT Pub. Date: Oct. 30, 2014

(65) Prior Publication Data
US 2016/0223450 A1 Aug. 4, 2016

(30) Foreign Application Priority Data
Apr. 22, 2013 (BR) ...................... 10 2013 009772 1

(51) Int. Cl.
*G01N 13/02* (2006.01)
*G01N 7/10* (2006.01)
(Continued)

(52) U.S. Cl.
CPC ............... *G01N 13/02* (2013.01); *G01N 7/00* (2013.01); *G01N 7/10* (2013.01); *G01N 33/246* (2013.01); *G01N 2013/0266* (2013.01)

(58) Field of Classification Search
CPC ............ G01N 13/02; G01N 7/00; G01N 7/10; G01N 33/246; G01N 2013/0266
(Continued)

(56) References Cited

U.S. PATENT DOCUMENTS 3,874,590 A * 4/1975 Gibson ................ A01G 25/167
137/78.3
3,910,300 A * 10/1975 Tal ....................... A01G 25/167
137/78.3
(Continued)

FOREIGN PATENT DOCUMENTS

BR      PI0004264 A    4/2002
BR      PI0803322 A2    6/2010
(Continued)

OTHER PUBLICATIONS

International Searching Authority, Written Opinion (English translation) for International Application No. PCT/BR2014/000128, dated Sep. 12, 2014, 8 pages, National Institute of Industrial Property, Brazil.
(Continued)

*Primary Examiner* — Marrit Eyassu
(74) *Attorney, Agent, or Firm* — Alston & Bird LLP

(57) ABSTRACT

The present invention provides a water tension sensor with a non-sintered core that allows batches of similar and standard sensors to be manufactured in a simple manner, for (Continued)

operation with air and with an air flow outlet, which sensor can be used to read water tension and trigger dripping. The sensor according to the invention is ideal for manually reading soil water tension and for automating irrigation systems based on a static pressure or gas propulsion mechanism.

53 Claims, 15 Drawing Sheets

(51) Int. Cl.
*G01N 33/24* (2006.01)
*G01N 7/00* (2006.01)

(58) Field of Classification Search
USPC .................................................. 73/64.51
See application file for complete search history.

(56) References Cited

U.S. PATENT DOCUMENTS

| | | | |
|---|---|---|---|
| 4,231,187 A * | 11/1980 | Greenbaum | A01G 27/04 47/39 |
| 4,837,499 A | 6/1989 | Scherer, III | |
| 5,179,347 A | 1/1993 | Hawkins | |
| 7,437,957 B2 | 10/2008 | Jobin et al. | |
| 7,631,545 B2 | 12/2009 | Skaling et al. | |
| 2003/0140690 A1* | 7/2003 | Faybishenko | G01N 15/0893 73/152.18 |
| 2008/0202219 A1* | 8/2008 | Schmidt | A01G 25/167 73/64.48 |
| 2009/0050214 A1* | 2/2009 | Shani | A01G 25/167 137/78.3 |
| 2009/0206853 A1 | 8/2009 | Hawkins | |
| 2013/0145829 A1* | 6/2013 | Gimenez Calbo | A01G 25/167 73/64.48 |
| 2014/0053633 A1* | 2/2014 | Caron | G01N 13/02 73/38 |

FOREIGN PATENT DOCUMENTS

| | | | | |
|---|---|---|---|---|
| DE | 102009014946 A1 * | 10/2010 | | G01N 13/02 |
| EP | 0489656 A1 * | 6/1992 | | G01N 33/24 |
| EP | 1183944 B1 | 4/2007 | | |
| WO | WO 1986/004212 A1 | 7/1986 | | |
| WO | WO 2009/024962 A2 | 2/2009 | | |
| WO | WO 2011/079367 A1 | 7/2011 | | |

OTHER PUBLICATIONS

Gimenez Calbo, Adonai, et al., "Gaseous Irrigation Control System: Description and Physical Tests for Performance Assessment," Bragantia, Campinas, 2006, p. 501-510, vol. 65, No. 3, Brazil.

International Searching Authority, International Search Report (ISR) and Written Opinion for International Application No. PCT/BR2014/000128, dated Sep. 12, 2014, 13 pages, National Institute of Industrial Property, Brazil.

Ridley, A.M. et al., "A New Instrument for the Measurement of Soil Moisture Suction", Géotechnique, 1993, pp. 321-324, vol. 43, No. 2, Institution of Civil Engineers, Great Britain.

* cited by examiner

WATER TENSION SENSOR, SYSTEM FOR CHARACTERISING AND CONTINUOUSLY MEASURING SOIL WATER, SYSTEM FOR INDICATING CRITICAL SOIL WATER TENSION AND IRRIGATION ROD

CROSS REFERENCE TO RELATED APPLICATIONS

This application is a National Stage application, filed under 35 U.S.C. § 371, of International Application No. PCT/BR2014/000128, filed Apr. 24, 2014, which claims priority to and the benefit of Brazilian Application No. 10 2013 009772 1, filed Apr. 22, 2013; the contents of both of which as are hereby incorporated by reference in their entirety.

BACKGROUND

Technical Field

The present invention provides a sensor and related instrumentation for reading and/or controlling water tension and can be applied in the agricultural sector and particularly in the filed or irrigation control and automation.

Description of Related Art

Tensiometer is an instrument to measure the force or tension with which the water is retained in soil and other substrates. The common tensiometer used for management of irrigation water, comprises a porous capsule having a cavity full of water hermetically connected to a vacuometer (Soil Science, v. 53, p. 241-248, 1942). Its working range is between zero and barometric pressure, but in practice it is mainly used between zero and 70 kPa.

The common tensiometer is also taken as a reference and research tool in various areas related to soil science and geomaterials such as physics and soil management, hydrology, geophysics, geotechnics, ecology and the environment. The porous capsule is used as a transduction element and for measuring the force with which water is held in the soil by reading the negative pressure of the water tension in a vacuometer. The major limitation of the common tensiometer is the fact that it is easily subject to the accumulation of air in the water contained within the porous capsule, which kept under negative pressure facilitates this accumulation of air and the response of the tensiometer increasingly slower until it loses its useful response capacity. Additionally, after maintenance, with the addition of water, removal of air and lid closure, there may be a delay in obtaining new valid readings.

Increasing the operating range and reducing the difficulties concerning maintenance of the common tensiometer have proven to be major motivations for the development of new instruments. Particularly desirable are new types of tensiometers and sensors for irrigation management which are more suitable for automation.

In order to increase its working range Ridley & Burland 1993 (GEOTECHNIQUE, V. 43, p. 321-324, 1993) developed a high-performance tensiometer for applications in geology and civil engineering that enables reading of up to 1500 kPa. The high performance tensiometer works similarly to the common tensiometer except that it features in the porous capsule, with high bubbling pressure, a low-volume cavity in which a tiny pressure transducer is inserted. Before operation, the high performance tensiometer is hydrated under a pressure greater than 4000 kPa, for about a day, within a pressure chamber. This pre-treatment is intended to dissolve all air bubbles that may act as initiators of the process of cavitation. It is, however, an unstable instrument, the reading of which is often interrupted by the sudden formation and expansion of air bubbles inside the cavity. The accumulation of air or embolism in the high-performance tensiometer has a much more serious effect than in the common tensiometer, because it is an instant response that occurs under negative module pressures much higher than barometric pressure.

To reduce the difficulties related to the task of opening the tensiometer and adding water ("flushing") without delaying the obtainment of a new valid reading, various solutions have been found. For example, document U.S. Pat. No. 7,631,545 discloses a tensiometer with a piston and spring system that makes it possible to remove air from the cavity porous capsule of the tensiometer, contained within an extension tube, with the aid of a simple procedure of adding water which is driven by rapid movement of the piston. Another more complex alternative to overcome this same problem of the common tensiometer is described in document U.S. Pat. No. 7,437,957 where the equipment operates in the range between 0 kPa and about 70 kPa and has an automatic mechanism for water injection to expel the air that accumulates in the cavity of the porous capsule. Additionally, in the tensiometer with a communication antenna according to document U.S. Pat. No. 7,631,545, the pressure transducer is placed adjacent to the porous capsule so there is no need to correct the insertion depth of the tensiometer into the ground.

Also with a view to reducing maintenance activities and increasing the reading scale of the common tensiometer, document DE102009014946 addresses a particular system for transducing the water tension in the ground in thermal conductivity of a porous medium, similar in principle to the system described by Oliveira (Pesq. Agropec. Bras. v. 34, p 14 7-1425, 1999). Accordingly, in document DE102009014946, the measure described is indirect and is performed with an instrument for measuring thermal conductivity of a porous tissue contained within the porous capsule. The reading of water tension of the ground is obtained by a non-linear measurement curve between the water tension in the ground and the thermal conductivity of the material. An additional capability of this type of system, the possibility of measuring the electrical conductivity of the ground is claimed. However, an important limitation of the system is the need for non-linear specific measurement for each sensor.

Under low water tensions the cavitation problem, that is, when the cavity of the tensiometer's porous capsule fills with air, is minor. This feature enabled the development of popular systems of domestic irrigation management such as the one described in document WO8604212. This document describes a system in which the water tension in the ground is used to decrease the throttle grip of a flexible tube through which the emission of irrigation water occurs. It is a simple system for automating irrigation, which is effective, for example, in keeping the soil of a vase always moist. It is, however, an extremely simplified system where there is no reading of the water tension in the substrate and adjustment is totally dependent on the sensitivity of the user.

For more accurate automatic irrigation management, applicable in greater water tensions, typically between 20 and 70 kPa, tensiometers equipped with piston and spring enable automatic adjustment of the soil-water tension as described in document U.S. Pat. No. 3,910,300. The limitation caused by air accumulation in the cavity of the porous capsule persists in this sense.

In order to overcome the need for maintenance and the narrow working range of the common tensiometers, the invention described in document U.S. Pat. No. 3,874,590 uses a material, nylon for example, which expands in the presence of water to control the opening of an overflow tube whenever the water tension exceeds a given critical value. It is an interesting concept, however, the embodiment requires individual measurement of the issuers and does not have an internal system of quantification and adjustment of the water tensions applied. Document WO2009024962 discloses a tensiometric system based on the hydration of a porous and expansive substrate, with issuer blockage. It is a system where it is possible to adjust the critical voltage irrigation tension in a vacuometer, from 20 to 70 kPa. The combination is relatively sophisticated and there is a possibility of integration of various sensors response/issuers for extensive management of irrigation applications. In addition to the sophistication that tends to make the system costly, there is also the limitation of the working tension range as in the common tensiometer.

The limitations of the common tensiometer have also motivated the development of electronic sensors for measuring the water content of soils to increase the efficiency of irrigation management work. Document U.S. Pat. No. 4,837,499 describes a sensor with a robust metal casing and a fibrous core that comes into balance with the water tension of the soil, allowing a non-linear evaluation between the capacitance and the soil moisture content, especially those with high levels of iron oxide, clay and organic matter. The response of this system, however, is influenced by soil salinity and requires a specific measurement for some types of soil (for example, organic soil, rich in clay with high contents of iron oxides, among others). Another example is reported in document US2009206853, which discloses a resistive sensor with enhanced responsiveness with respect to the sensor of document U.S. Pat. No. 5,179,347 by the same author, thanks to the use of a special coating. In this soil moisture sensor, a conductive metal housing perforated for water permeation, gives greater robustness to sensor while a filter liner protects and promotes the water balance of gypsum core with two electrodes. The electrical conductivity between the electrodes provides moisture reading and the system works between water tensions of 50 to 200 kPa, but is strongly influenced by salinity and by temperature.

New systems for measuring soil-water tension which depend on the surface tension of the water begin to gain importance because they are practically immune to variations in soil salinity and additionally feature minor response variation based on the current temperatures in cultivation environments.

One system based on this property is the dihedral sensor of document WO2011079367. It is a system with applications for determining the components of the potential and of the water activity. In the dihedral sensor, as the technical name suggests, the soil-water tension is measured in accordance with the position of the meniscus water/air inside glass plates or flat porous elements fixed at an angle (dihedral) based on a point of contact at the apex. One of the main applications of dihedral sensors is to measure the soil-water tension with the aid of porous elements and optical, electrical or pneumatic systems. It is a linear response system and has great potential for water irrigation management purposes. In the pneumatic application, a flow of air under diminished pressure, typically from 1 to 2 kPa, is locked inside the sensor whenever the water tension drops and the water fills the volume of the plate in the air inlet orifice region. To be durable, the air used in these pneumatic embodiments must be free of impurities and applied with low flow.

In a more restricted use, the Irrigas sensor of document BR0004264 is also based on the surface tension of water, but when used in pneumatic mode it operates for long periods, even in regions with highly polluted air. In the Irrigas sensor, the outer layers of porous capsule naturally separate the oil from ambient air pollution, which in very small amounts does not adversely affect the working of the sensor, at least within a useful life span of 3 years. In the Irrigas system, porous capsules having the cavity filled with air and no water are subjected to an air pressure (p) and the water pressure in the soil is measured as the difference between the parameter pB (bubbling pressure) and the p reading. For irrigation management with the Irrigas system, porous elements with appropriate pB values are prepared in the industry to meet the different demands of irrigation management.

In the processes of measuring bubbling pressure in drying or desorption, porous capsules are placed in the initial condition as measured by a wetting process by immersion in water until they stop sucking up water from the environment, which can be checked by weighing. In measuring the bubbling pressure of this porous capsule submerged in water, the air pressure in the capsule cavity slowly increases and a reading is taken of the lowest pressure that causes air bubbling. This pressure is the bubbling pressure in desorption or in drying, and in the particular case of the Irrigas sensors, it is metaphorically called critical tension. The reason is that this pressure can also be measured with the aid of a Richards pressure chamber, measuring in which soil-water the capsule becomes permeable to air. The values measured with bubbling and in the Richards chamber are experimentally equal (Bragantia, V. 65, n. 3, p. 501-510, 2006). Commercially, for this technical reason the Irrigas sensors are sold specifying the critical pressure and a very simple method of determining in the field when the soil-water exceeds this value. Farmers consequently have used capsules with bubbling pressure, critical tension, equal to agronomically-recommended water tension values for irrigation of different crops.

The Irrigas sensor, as described in document BR0004264, has relevant technical problems in the manufacture of porous elements sintered with finely adjusted bubbling pressure. Obtaining consistent and adequate products imposes industrial difficulties even when the mineral particles are well adjusted in terms of composition, particle size and sintering temperature. Thus, even with all these precautions, it is common to obtain variations of more than 20% in the bubbling pressure or critical pressure of these sensors when they are removed from the oven. Accordingly, commercializing sensors with accurate properties, for example, with a 4% error in the critical tension (eg 25±1 kPa), the measurement of the sensors needs to be made individually in a Richards chamber (Soil Science, v. 51, p. 3'7'7-386, 1941). The individual measurement of sensors, however, is a slow and costly process. The Irrigas also has other types of industrial difficulties and has so far undergone technical difficulties to produce sensors with critical tensions under 10 kPa, which are important in the cultivation of plants in substrates, and with critical tensions over 150 kPa, mainly designed for irrigation management with controlled water deficits at specific stages of crop development.

A third problem of the Irrigas sensors is of a non-industrial nature and is caused by air leaking out of the porous capsules and cannot be used for specialized irrigation management tasks. This limitation, for example, complicates the use of the atmodripping system described in document BR0803322, a system in which an air flow that may come from the sensor is used to raise the water above a set level (propulsion). The atmodripping enables not only dripping over a wide range of flows, starting from very low values of around 0.060 liters/hour up to more than 4 liters/hour, with virtually no risk of clogging of the emitters. It would therefore be desirable to develop a more compatible sensor to facilitate irrigation management by the atmodripping system.

In this context, the present invention provides the water soil tension sensor with a non-sintered core that allows batches of similar and standard sensors to be manufactured in a simple manner, for operation with air and with an air flow outlet utilizable for reading water tension and for trigger dripping. The sensor according to this invention is ideal for manually reading soil-water and for automating irrigation systems by pressostatic or gas-driven mechanisms.

BRIEF SUMMARY

The present invention refers to the water tension sensor (6) in the ground (7) and/or in similar materials comprising such sensor, a non-sintered core (2) enveloped by a porous support element (1), said core limited at its ends by porous blocks (3) connected to an air inflow duct (4) and an air outflow duct (5).

The invention also refers to a system (80) for characterization and continuous readings of soil-water (7) said system comprising:
f. a water tension sensor (6) in the soil,
g. cylinder of compressed air (10),
h. a shutoff valve (11),
i. a restrictor (12),
j. a pressure transducer (13), The invention further relates to a system (60) for indicating critical soil-water tension (7) said system (60) comprising:
j. a bubbling display (37),
k. mineral oil (39),
l. a source of compressed air,
m. a water tension sensor (6) in the soil,
n. a flat porous element (38)
o. resin (41)
P. an air inflow duct (42A) of the sensor (6)
q. an air outflow duct (42B) of the sensor (6), and
r. a restrictor (12), Additionally, the invention also refers to an irrigation rod (17) said device comprising:
g. a water tension sensor (6) in the soil
h. an air inflow duct (33),
i. a chamber (70) containing a float (21), a lid (28) endowed with an air exhaust orifice (32) and the water inflow duct (22),
j. an air outflow duct (34),
k. a water outflow duct (30), and
l. a waterproof plate (24).

The present invention also refers to a soil-water sensor (110) of non-sintered core with light reflection reading comprising:
f. a porous element (1);
g. core (2) of non-sintered particles;
h. cover (46);
i. lamp (47); and
j. light sensor (48).

The invention further refers to a soil-water sensor (120) of non-sintered core to measure soil-water by light transmission comprising:
f. a porous element (1);
g. non-sintered core (2) arranged as a laminar aggregate;
h. cover (46);
i. lamp (47); and
j. light sensor (48).

Additionally, the invention refers to an irrigation rod (140) having automated thermal pressurization with a pneumatic soil-water sensor comprising:
s. Inflow duct (66);
t. differential pressure valve (141);
u. core sensor (6) installed in the soil (7);
v. air inflow duct (4);
w. solar collector (67);
x. high fitting (51);
y. middle chamber (61);
z. pressure relief in the middle chamber (61),
aa. air flow restrictor (12);
bb. tubular water flow restrictor (55)
cc. pin (64) between the clamping diaphragm (59);
dd. closing diaphragm (62);
ee. disc (60);
ff. overflow duct (56),
gg. raised irrigation duct (68);
hh. water flow restrictor 143);
ii. fitting (65) of the side chamber (58); and
jj. foot (79) for fastening the irrigation rod to the ground.

The present invention also refers to a molded restrictor (143) with water flow resistant to the increase in pressure and with cleaning by backwashing comprising:
g. water inflow duct (66);
h. opening (75)
i. closing diaphragm (62),
j. flow setting channel (71);
k. compression channel (74); and
l. support grooves (70).

The invention also refers to the water irrigation rod (150) with adjustable duct angle comprising:
q. pressure divider (142);
r. angle duct (76);
s. inflow duct (66);
t. lower chamber (63);
u. molded restrictor (143) for water flow;
v. lower chamber (63);
w. middle chamber (61);
x. closing diaphragm (62);
y. side chamber (58);
z. middle chamber (61);
aa. clamping diaphragm (59);
bb. disc (60);
cc. pin (64);
dd. overflow duct (56);
ee. fitting (65); and
ff. foot (79) for fastening the irrigation rod to the ground.

Additionally, the invention refers to an automatic irrigation rod (160) with pressurization by hanging water column controlled by pneumatic soil-water sensor comprising:
o. inflow duct (66);
p. lower chamber (63);
q. molded water flow restrictor (143);
r. sensor (6) with air inflow duct (4) and air outflow duct; high fitting (51);
s. middle chamber (61);
t. differential pressure valve (141);
u. overflow duct (56);

v. side chamber (58);
w. clamping diaphragm (59);
x. disc (60);
y. closing diaphragm (62);
z. pin (64);
aa. tensioning tube (78); and
bb. foot (79) for fastening the irrigation rod to the ground.

The present invention also refers to a dual pneumatic soil-water sensor (180) with aggregate response through the air inflow duct and air outflow duct comprising:
h. outer porous element (1);
i. upper sensor (72);
j. lower sensor (73);
k. non-sintered core (2);
l. air inflow duct (4);
m. porous block (3);
n. air outflow duct (5).

Figure 1:
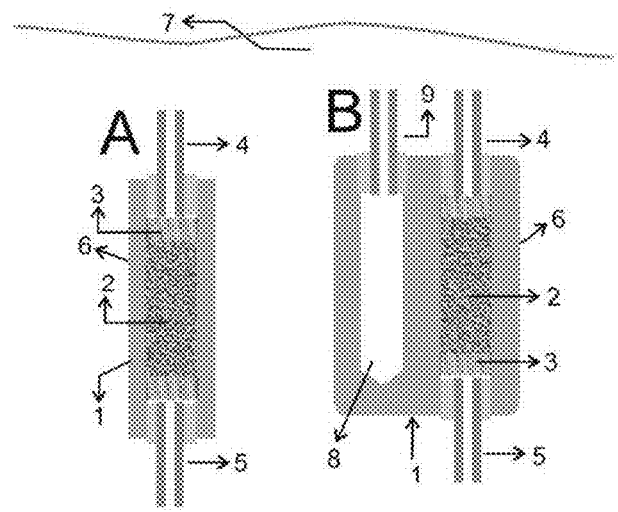
FIG. 1: A—Water tension sensor (6) in the soil wherein (1) is the porous support element, (2) non-sintered core, (3) porous blocks, (4) air inflow duct, (5) air outflow duct, (7) solo. B—Water tension sensor (6) in the soil endowed with measuring device wherein (1) is the porous support element, (2) non-sintered core, (3) porous blocks, (4) air inflow duct, (5) air outflow duct, (7) solo, (8) measuring cavity, (9) measuring duct.

B— Dual-depth soil-water sensor (180) with aggregate response through the air inflow duct (4) and air outflow duct (5) comprising upper sensor (72), lower sensor (73), porous center-communicating block (3), upper sensor (72) and lower sensor (73), porous element (1).

DETAILED DESCRIPTION OF VARIOUS EMBODIMENTS

The water tension sensor (6) in the soil referred to in the present invention is designed for irrigation water management and may readily be manufactured in batches of standardized sensors and with optimized working range. It is an ideal sensor for applications that monitor humidity or soil-water and substrates in general. The sensor works by pneumatic mechanism, and may be used both for manual readings as for readings with data collector. Its water tension readings can be used to define when and how much to irrigate, and also to automate irrigation. Additionally, since the sensor can work without air dissipation, it is ideal for manufacturing irrigation emitters called irrigation rods, which act automatically by pneumatic propulsion generated by an air flow.

Prepared in a porous body element (1) with high bubbling pressure, air impermeable, when wet, the water tension sensor (6) in the soil (7) contains hydrophilic, hard and compacted particles with known dimensions to measure linearly the soil-water tension between zero and the bubbling pressure of the particles that make up the non-sintered core (2). The sensor is suitable for standardized manufacturing to meet specific ranges of water tension needed in irrigation management applications. The sensor (6) enables pneumatic measures of the water tension in the soil without the loss of air flow, which facilitates the activation of new water emitters called irrigation rods. In these emitters, the air flow propels the irrigation, which ceases as soon as the wetting front moistens the sensor (6) and blocks the air flow. The sensor according to this invention may also be used in the manufacture of portable and stationary systems for reading and acquisition of water tension data. The working range of these systems is between zero and the module of the critical water tension, or bubbling pressure.

The water tension sensor (6) of the present invention comprises a non-sintered core (2) enveloped by a porous support element (1) and said core (2) is limited at its ends by elastic and preferably foam hydrophobic blocks (3) connected to an air inflow duct (4) and an air outflow duct (5).

In this sensor (6), the passage of an air flow inside the porous element (1) and through the core (2) is made possible by means of a pressure dissipation which is the function of the water tension in the soil and which becomes null above a given critical value characteristic of the particles used as filling for the core (2) (equation 1).

FIG. 1A shows the respective sensor (6). The non-sintered core (2) of the sensor (6) of the invention is preferably made of hydrophilic material. More preferably, the hydrophilic material of which the core (6) is made features a contact angle near to zero and less than 26 degrees, that is, with the cosine of the contact angle greater than 0.9. Various types of materials can be used to constitute the core (2) of the sensor (6) of the invention. Such materials include glass spheres and corundum. The porous support element (1) of the sensor (6) of the invention is also made preferably of hydrophilic material, said material, also preferably, featuring a cosine of contact angle greater than 0.9. Various materials can be used to constitute the porous support element (1) of the sensor (6) of the invention. Such materials include ceramic, gypsum and pervious concrete. Also part of the water tension sensor (6) of the present invention, the porous blocks (3) that limit their ends are made preferably of porous, elastic and preferably hydrophobic materials, such as foams with bubbling pressure lower than that of the core material so as not to obstruct the air flow. For the water tension sensor (6) of the invention to work accurately in the soil (7), the porous support element (1) must have, preferably, at least, a bubbling pressure 4 times greater than the critical tension value of the non-sintered core (2). From a practical point of view, for water tension sensors that operate in the range from zero to 150 kPa, it is desirable to use porous elements with bubbling pressure between 600 and 1200 kPa, whenever response speeds lower than 15 minutes are not required in the technical applications.

In the water tension sensor of the invention, hydrophilic particles, with uniformity, hardness and stability, such as corundum or glass spheres, form the core (2) accommodated within a porous element (1), which is a solid body and with high bubbling pressure. The porous blocks (3) maintain the compacted core particles (2) in stabile position, regardless of being dry or containing water filling the interstices. Strictly speaking, the porous blocks (3) are expendable, for example, when the sensor is a U-shaped construction. Preparing the sensor without the porous blocks, however, is not recommendable, because it is important to keep the non-sintered particles of the sensor firmly positioned. Preferably, the two porous blocks (3) should have critical tension lower than 2.0 kPa, so as not to cause errors in the readings of water tension of very wet soils.

The porous element (1) with high bubbling pressure, which is the body of the sensor, assures air impermeability through its walls, while kept in equilibrium with soils under water tension lower than the its bubbling pressure. As a result, an air flow introduced into air inflow duct (4) of the porous element (1), under equilibrium condition, can be forced through the air outflow duct (5) by dissipation of air pressure p depending on the water tension in the soil (7) according to equation 1 below:

$$Ts = Pb - p \qquad \text{equation 1}$$

wherein Ts is the water tension in the soil (kPa), Pb is the air pressure (kPa), measured in relation to barometric pressure, applied to force the bubbling through the core (2) of the sensor (6) immersed in water and p is the difference in air pressure between the air inflow duct (4) and the air outflow duct (5) of the tubular core sensor (6). In other words p is the pressure dissipation of the sensor (6) induced by the passage of a given air flow through its core (2) impregnated with water. It is important to note that the bubbling pressure of the porous element (1) and of the porous blocks (3) does not enter into equation 1. Firstly because it acts as an impermeable wall, given its high critical tension and secondly because it has a much lower critical tension than the non-sintered particles of the core (2).

As an alternative arrangement of the sensor (6) of the invention, it is possible to cite the additional presence of a measuring device adjacent to said sensor (6). Said device comprises a measuring cavity (8) surrounded by a porous support element (1) and by a measuring duct (9) as can be noted in FIG. 1B. Water, for example, can be added to this measuring cavity (8), with the aid of a syringe, to reduce the water tension in the sensor to zero. Next, the water tension of the sensor (6) is adjusted by applying partial vacuum during reading. This procedure dispenses with the use of slow, sophisticated and costly measurement instruments, and can be used whenever the critical tension Pb parameter of the sensor (equation 1) is of a magnitude lower than the local barometric pressure module.

The porous support element (1) of the respective device is made preferably of hydrophilic material, this material, also preferably, featuring a cosine of the contact angle greater than 0.9. Various materials can be to constitute the porous support element (1) of the measuring device adjacent to the sensor (6) of the invention. Said materials include ceramic, gypsum and pervious concrete.

The present invention also refers to a system (80) for characterization and continuous readings of soil-water (7), comprising:
f. a water tension sensor (6) in the soil,
g. cylinder of compressed air (10),
h. a shutoff valve (11),
i. a restrictor (12),
j. a pressure transducer (13).

The water tension sensor (6) in the soil of the respective system (80) comprises a non-sintered core (2) enveloped by a porous support element (1), said core limited at its ends by porous blocks (3) connected to an air inflow duct (4) and an air outflow duct (5). The non-sintered core (2) of the sensor (6) component of the system (80) is preferably made of hydrophilic material. More preferably, the hydrophilic material component of the core (2) has a cosine of the contact angle greater than 0.9. Various types of materials can be used to constitute the core (2) of the sensor (6) component of the system (80) of the invention. Said materials include glass spheres and corundum. The porous support element (1) of the sensor (6) component of the system (80) is also preferably made of hydrophilic material, said material featuring, also preferably, cosine of the contact angle greater than 0.9. Various materials can be used to constitute the porous support element (1) of the sensor (6) component of the system (80). Said materials include ceramic, gypsum and pervious concrete. The porous blocks (3) that limit the ends of the sensor (6) component of the system (80) are preferably made of materials selected from among elastic porous materials and, preferably, hydrophobic.

For the sensor (6) component of the system (80) of the invention to work correctly, the porous support element (1) must have, preferably, at least, a bubbling pressure 4 times greater than the critical tension of the non-sintered core (2).

In said system (80) of the invention, (FIG. 2A) the air inflow duct (4) in the sensor (6) connects to the cylinder of compressed air (10) preferably by way of an air duct (50). Still within the system of the invention (80) the shutoff valve (11), the restrictor (12) and the pressure transducer (13) are connected to the air duct (50).

To use the core sensor (6) in gas tensiometry mode, that is, in the system (80) for characterization and continuous readings of soil-water (7) of the invention, the non-sintered particles of the core (2) (FIG. 2A) must be firmly fastened between the porous blocks (3) so that they do not move, even under the action of air pressures of up to 500 kPa. In this system (FIG. 2A), the sensor (6) with the non-sintered particles retaining water by capillary action continuously measures the water tension according to pressure dissipation (p), of the forced air flow through the core (2). This is the simplest way by which the water tension in the soil (7) modulates the difference in pressure whose measurement is used to apply equation 1 and estimate the water tension.

For operating the system (80), the sensor (6) is coupled through a restrictor (12), made of copper, glass or plastic, which adjusts the air flow, typically around 0.5 ml/min. This air flow measured at local barometric pressure is obtained stably and with a variation less than 25%, when the difference in air pressure applied through resistance is greater than four times the Pb value.

Another important aspect in this system is that the p value is very slightly influenced by the increase in the air flow, such that a ten-fold increase in air flow, for example, an increase from 0.5 ml/min to 5 ml/min, causes an increase in p pressure of less than 5%. To regulate the input pressure, a cylinder of compressed air (10), or an air compressor, is used, for example, with a pressure setting of 400 kPa, over barometric pressure, and a shutoff valve (11), which is kept open during the readings.

Using larger air flows through the core (2), the reading is faster, but high, dry air flows may cause drying errors, which may inflate the reading. Thus, the value of the air flow used in soil-water measurements with the sensor (6) must be proportional to the cross-section of the core (2) and must have a non-linear relationship with the size of the core particles (2) which retain the water by capillary action. Consequently, assuming there is no water permeability limiting the porous element (1), greater air flows can be applied as and when the diameter of the core (2) and the size of their non-sintered particles increase. For safety, however, it is always desirable to use reduced air flows, which is made easier when working with low dead volumes of air in the system. Low dead volumes (<2 ml) can be achieved, for example, using tubes and fittings with small internal diameter, typically around 0.2 mm.

Figure 2:
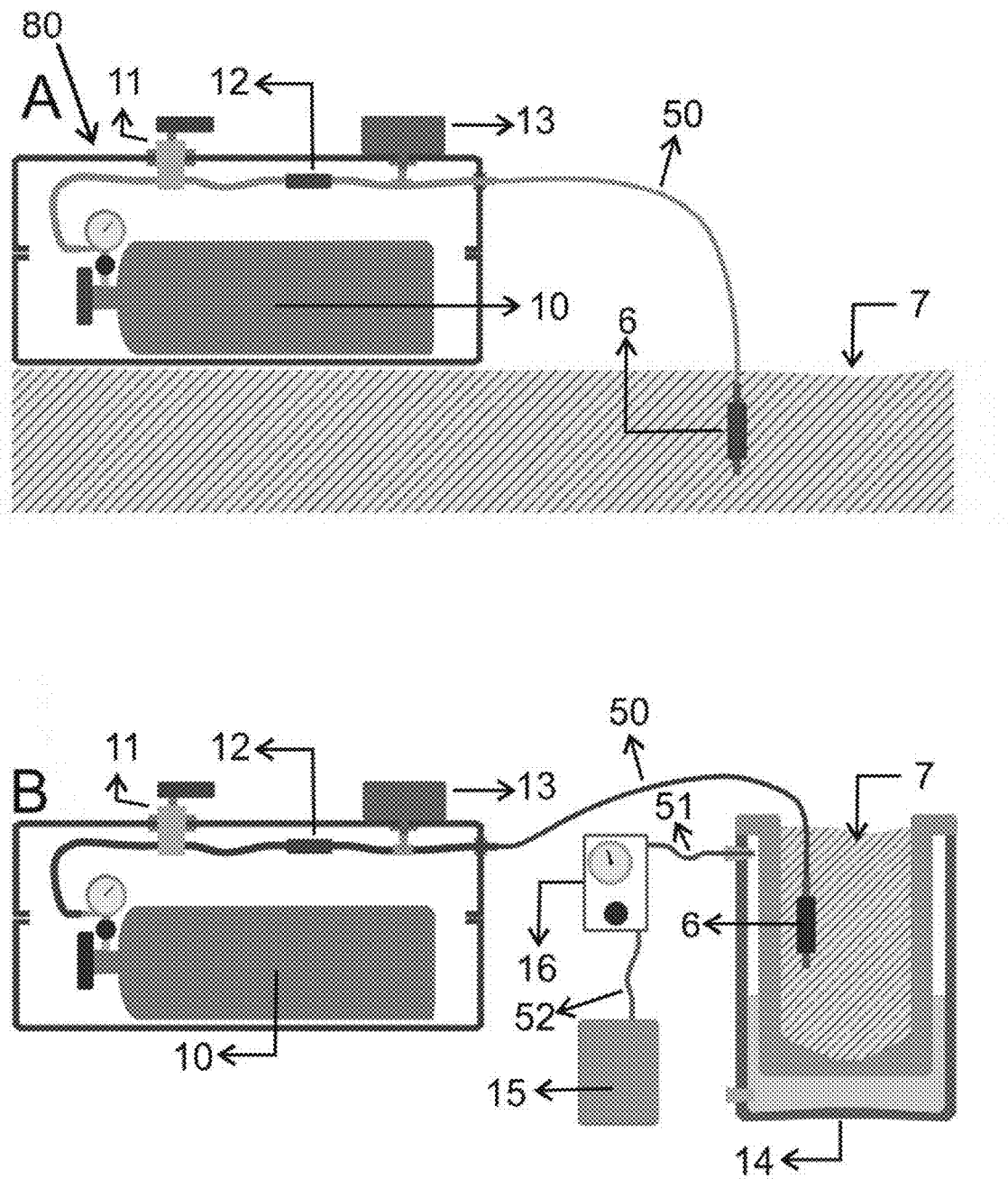
FIG. 2: A—System (80) for characterization and continuous readings of soil-water wherein (6) is the water tension sensor in the soil, (10) cylinder of compressed air, (11) shutoff valve, (12) restrictor, (13) pressure transducer, (50) air duct. B—System for characterization and continuous readings of soil-water added with equipment for calibrating the sensor (6) wherein (10) is the cylinder of compressed air, (11) shutoff valve, (12) restrictor, (13) pressure transducer (14) Richards chamber, (15) vacuum pump, (16) vacuum regulator, (50) air duct, (51) vacuum duct, (52) intermediary duct.

In a preferred embodiment (FIG. 2B) the system (80) of the present invention additionally provides devices responsible for calibrating/characterizing the water tension sensor (6). The respective devices comprise a vacuum pump (15), a vacuum regulator (16) and a Richards chamber (14). In the respective preferred embodiment, the vacuum regulator connects to the vacuum pump (15) and to the Richards chamber through, respectively, an intermediary duct (52) and a vacuum duct (51). In this preferred embodiment (FIG. 2B), the water tension in the soil for calibrating and characterizing the sensor (6) can be adjusted, for example, by the use of partial vacuum, using a Richards chamber (14). In the system of FIG. 2B, the Richards chamber (14) is an auxiliary item that allows adjustments in the soil-water (7) for measurements of the sensor (6) of this invention. In the illustrated case, the Richards chamber is negative pressure, and leaves the soil continuously exposed, which facilitates measurement of the sensors (6) in the range between 0 and 80 kPa. The water tension of the soil contained in the Richards chamber (14) is, on balance, equal to the partial vacuum adjusted by the vacuum regulator (16) partially linked to the vacuum pump (15).

FIG. 3A shows the linear response behavior, with the slope near to 1.0, between the water tension in the soil and the reduction da gas pressure indicated by the system (80) containing the Richards chamber (14), the vacuum pump (15) and the vacuum regulator (16). In the sensor (6), a continuous flow of gas molecules at 0.5 ml/min traverses the non-sintered core (2) and enables a reading of the water tension in the measurement illustrated in FIG. 2B. FIG. 3B shows a typical response counted from the moment of opening the shutoff valve (11), during a soil-water (7) reading with the non-sintered sensor (6), previously set. The solid arrow represents a reading of pressure dissipation taken in desorption or drying mode and the dashed arrow represents a reading of the pressure dissipation caused by the air flow, taken in sorption or wetting mode.

As can be noted in FIG. 3B, there is an increase in initial pressure, followed by the occurrence of a peak while the core particles (2) undergo dehydration. After the peak, accommodative hysteresis, and stabilization at a slightly lower pressure value than the peak in a process of slight wetting. The readings shown in FIG. 3A were taken after stabilization of pressure (p), as illustrated by the dashed arrow in FIG. 3B. The increase in pressure, illustrated in FIG. 3B, initially occurs without air flow through the sensor (6), in linear phase, then it involves air exhaust, reaches a maximum value (solid arrow) and finally decreases and stabilizes (dashed arrow).

A relevant detail relating to equation 1 is that the Pb parameter for the core particles (2) has slightly different values, when measured in drying mode (solid arrow—FIG. 3B), start of bubbling, and in wetting mode, when it passes from greater bubbling pressure to lower pressure (dashed arrow—FIG. 3B).

Figure 3:
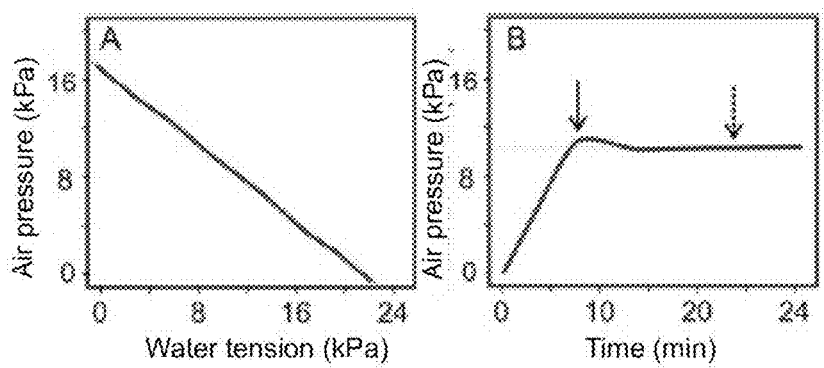
FIG. 3: A—Illustration of a typical air pressure reading curve in response to the adjusted soil-water (7) with a Richards chamber (14). B—Typical response counted from the time of opening the shutoff valve (11), during a soil-water (7) reading with the previously balance water tension sensor (6) in the soil (7). The solid arrow represents the pressure dissipation Reading taken in desorption or drying mode and the dashed arrow represents the reading of the pressure dissipation reading caused by the air flow, taken in the sorption or wetting mode.

The illustrations contained in FIG. 3 are valid for calibrating a batch of sensors (6) prepared with the same particles in a given particle size specification. Consequently, curves of this type are characteristic and representative of the sensors (6) of the batch, prepared with said particles, even if they have different dimensions and shapes, or are accommodated in different types of porous elements (1). For example, miniature core sensors (6) or larger core sensors to facilitate contact and the balance of water tension with the soil (7). All have the same response, provided they are used with air flow per area unit of the sufficiently small core (2), for example, 0.5 ml/(min·cm2).

Figure 4:
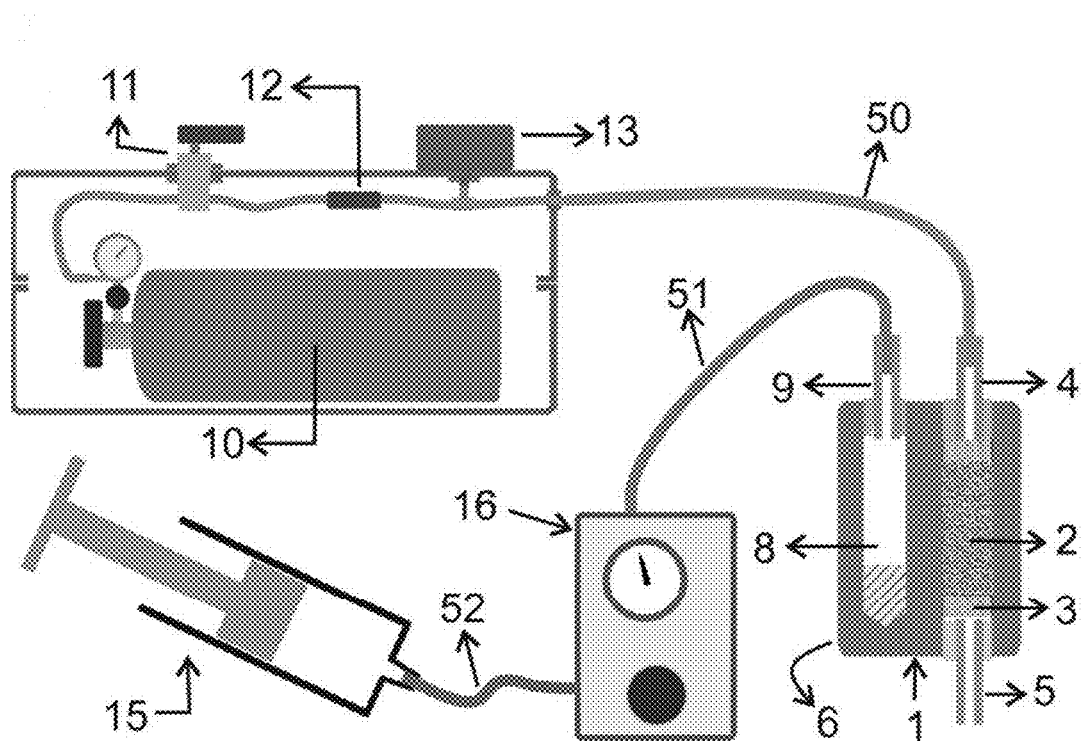
FIG. 4: Calibration system of the water tension in the water tension sensor (6) in the soil (7), previously moistened by water immersion effected by partial vacuum regulation with a vacuum pump (syringe) (15) wherein (1) is the porous support element, (2) non-sintered core, (3) porous blocks, (4) air inflow duct, (5) air outflow duct, (6) water tension sensor, (7) soil, (8) measuring cavity, (9) measuring duct, (10) cylinder of compressed air, (11) shutoff valve, (12) restrictor, (13) pressure transducer, (16) vacuum regulator.

The procedure for characterizing and measuring the sensor (6) is simpler when it contains a measuring cavity (8), as illustrated in a preferred embodiment of the invention shown in FIG. 4. With the measuring cavity, whenever Pb for the core (2) is less than barometric pressure, the use of the Richards chamber (14) for measurements is dispensable. This simplicity exists because the balance of water tension (T) can be induced in minutes while stabilization is accompanied by continuously reading the sensor. The preferred embodiment of FIG. 4 shows the measurement of the water tension in the sensor (6), previously immersed in water, made by partial vacuum regulation with a vacuum pump (15) and a vacuum regulator (16), linked to the measuring duct (9) of the measuring cavity (8) of the sensor (6). The measuring cavity (8) enables measurement of sensors with porous element of high critical tension without using the Richards chamber (14). The other components not described in FIG. 4 are equal to those previously considered in FIG. 2A.

In FIG. 4, a vacuum pump (15) as simple as a syringe can be used. Prior to setting the water tension in the sensor, it can be immersed, or else can be wetted by introducing water into the cavity with the aid of this syringe. Then the water tension is adjusted by partial vacuum in the cavity.

The use of the measuring cavity (8) for fast calibration of humidity and water tension sensors is very practical for core sensors. Additionally, the benefit of the measuring cavity can also be extended to other types of sensors, such as the Irrigas and the dihedral sensor. The necessary condition is that these sensors include a measuring cavity (8) and use porous elements of high critical tension, such that the water tension may be adjusted as described previously. The functionality of the measuring cavity (8) can be applied to any type of water tension or soil humidity sensor.

The present invention also refers to a system (60) for indicating critical irrigation tension. The respective system (60) comprises:
j. a bubbling display (37),
k. mineral oil (39),
l. a source of compressed air,
m. a water tension sensor (6) in the soil,
n. a flat porous element (38)
o. resin (41)
P. an air inflow duct (42A) of the sensor (6)
q. an air outflow duct (42B) of the sensor (6) and,
r. a restrictor (12), The water tension sensor (6) in the soil of the respective system (60) comprises a non-sintered core (2) enveloped by a porous support element (1), said core limited at its ends by porous blocks (3) connected to an air inflow duct (4) and an air outflow duct (5). The non-sintered core (2) of the sensor (6) component of the system (60) is preferably made of hydrophilic material. More preferably, the hydrophilic material component of the core (2) has a cosine of the contact angle greater than 0.9. Various types of materials can be used to constitute the core (2) of the sensor (6) component of the system (60) of the invention. Said materials include glass spheres and corundum. The porous support element (1) of the sensor (6) component of the system (60) is also preferably made of hydrophilic material, said material featuring, also preferably, cosine of the contact angle greater than 0.9. Various materials can be used to constitute the porous support element (1) of the sensor (6) component of the system (60). Said materials include ceramic, gypsum and pervious concrete. The porous blocks (3) that limit the ends of the sensor (6) component of the system are preferably made of materials selected from among elastic porous materials and, preferably, hydrophobic.

For the correct operation of the sensor (6) component of the system (60) of the invention, the porous support element (1) must have, preferably, at least, a bubbling pressure 4 times greater than the critical tension value of the non-sintered core (2). Values less than four times the critical tension value of the core may facilitate side leakage of air through the porous support element (1), which occurs if the dry soils to the point of attaining tensions various times higher than the critical tension of the non-sintered core (2).

In said system (60) the restrictor (12) is an air flow restrictor and the bubbling display (37) is made of glass, in which mineral oil (39) is kept within the flat porous element (38) fastened in dihedral against the glass plate of the bubbling display (37) with a resin (41). An orifice in the dihedral (40) conveys the air coming from the water tension sensor (6) through the air outflow duct of the sensor (42B), when the soil is dry. Establishing this indicator of critical irrigation tension assures that the oil always remains under the bubbling display (37). The volume of oil in this dihedral bubbler is adjusted by adding oil to the porous element with a dropper. Preferably, on the orifice in the dihedral (40), the distance between the flat porous element (38) and glass plate of the bubbling display varies between 60 and 90 µm. Even more preferably, the distance is 75 µm.

Figure 5:
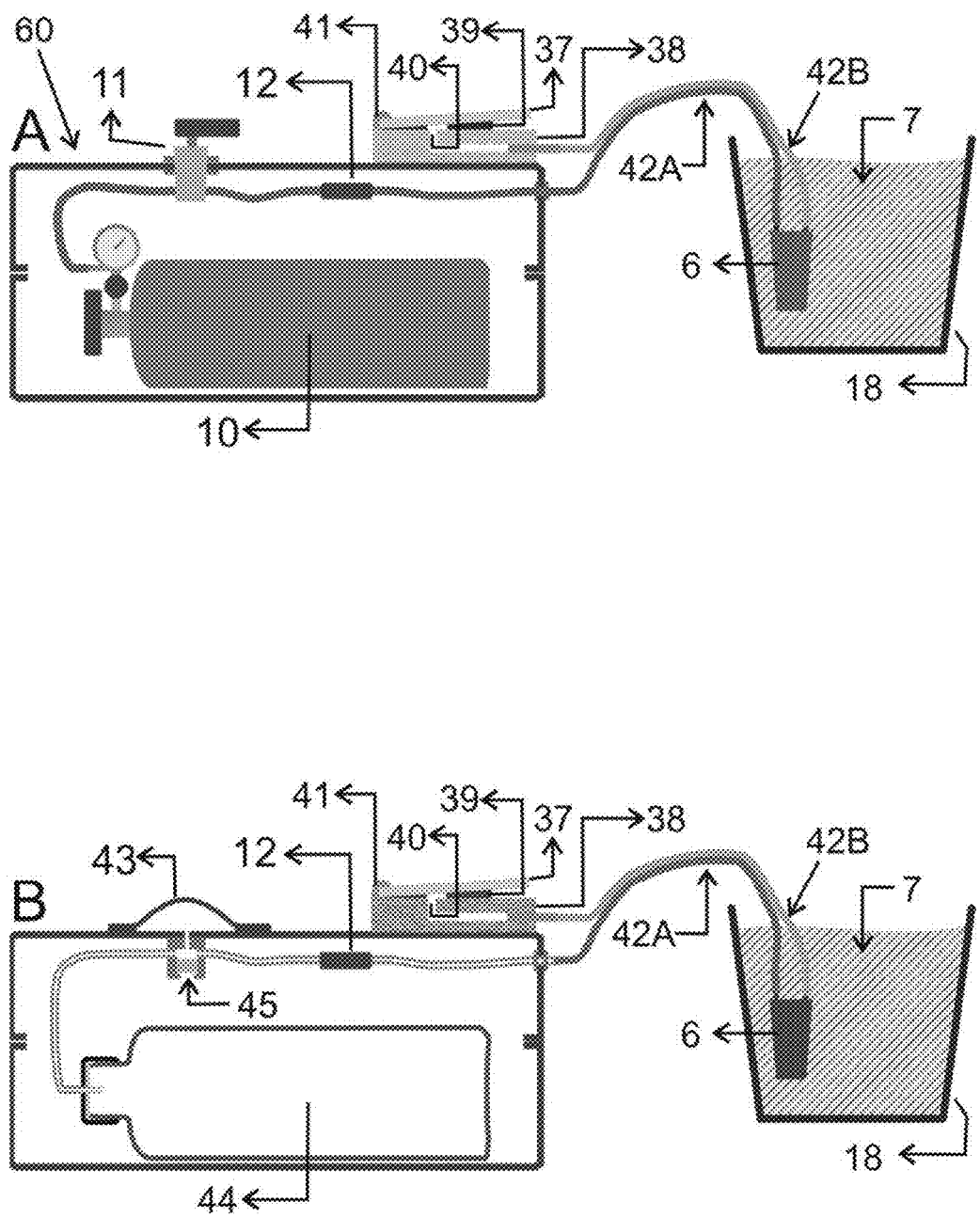
FIG. 5: A—System (60) for indicating critical soil-water tension (7) wherein (6) is the water tension sensor in the soil, (7) soil, (10) cylinder of compressed air, (11) shutoff valve, (12) restrictor, (18) vessel, (37) bubbling display, (38) flat porous element, (39) mineral oil, (40) dihedral, (41) resin, (42A) air inflow duct of the sensor, (42B) air outflow duct of the sensor. B—System for indicating the critical soil-water tension (7) wherein (6) is the water tension sensor in the soil, (7) soil, (12) restrictor, (18) vessel, (37) bubbling display, (38) flat porous element, (39) mineral oil, (40) dihedral, (41) resin, (42A) air inflow duct of the sensor, (42B) air outflow duct of the sensor, (43) rubber bulb, (44) reservoir, (45) one-way valve.

In a preferred embodiment of said system (60) shown in FIG. 5A, the source of compressed air is a cylinder of compressed air (10) or an air compressor. In this preferred embodiment the system (60) further comprises a shutoff valve (11). For the operation of the system, the pressure outlet must be set. Preferably, the pressure outlet is set between 1 and 4 kPa. Even more preferably, the pressure outlet is set at 3 kPa. The respective pressure of 3 kPa of air is small and is not sufficient to force the air through the water that impregnates the porous core (2) made by hydrophilic particles, except when the water tension of the soil is already near to or greater than the parameter Pb (equation 1).

The blockage of the air flow, perceived as the end of bubbling, indicates that the soil is moist and the water tension in the soil is reduced. On the contrary, in dry soil, bubbling occurs because the water tension in the soil is greater than the characteristic critical value of the sensor (6).

In another preferred arrangement of the system (60) shown in FIG. 5B the system (60) indicating critical irrigation tension is simpler and lighter, by removing the cylinder of compressed air, or the air compressor. In this case the pressure is generated by manually squeezing the rubber bulb (43) and the limitation of maximum pressure is defined with the aid of the reservoir (44) to produce the compressed air, and the pressure outlet is preferably set between 1 and 4 kPa. Even more preferably, the pressure outlet is set at 3 kPa. A one-way air inlet valve (45) enables repeat manual drive. The respective air pressure (1 to 3 kPa) is small and is not sufficient to force the air through the water impregnating the porous core (2) made by hydrophilic particles, except when the water tension of the soil is already near to or greater than the parameter Pb (equation 1).

The blockage of the air flow, perceived as the end of bubbling, indicates that the soil is moist and the water tension in the soil is reduced. On the contrary, in dry soil, bubbling occurs because the water tension in the soil is greater than the characteristic critical value of the sensor (6).

For irrigation management, the sensor (6) is preferably installed to half the effective depth of the root system, while ducts 42A and 42B can be hung with the end hanging on a post to prevent the entry of water. To assess whether the irrigation was adequate and is not being restrictive to exploitation of the soil by the root system, other core sensors (6) can be installed at a depth twice greater than that used to indicate when to irrigate, that is, at the effective depth of the root system, where about 80% of the roots are contained.

Measuring the system (60) for indicating critical irrigation tension is of a discrete nature and defines whether the soil is below or above a critical water tension value. This data is useful and practical because there are defined values of critical water tension for irrigation management in most plant/substrate/environment systems.

Figure 6:
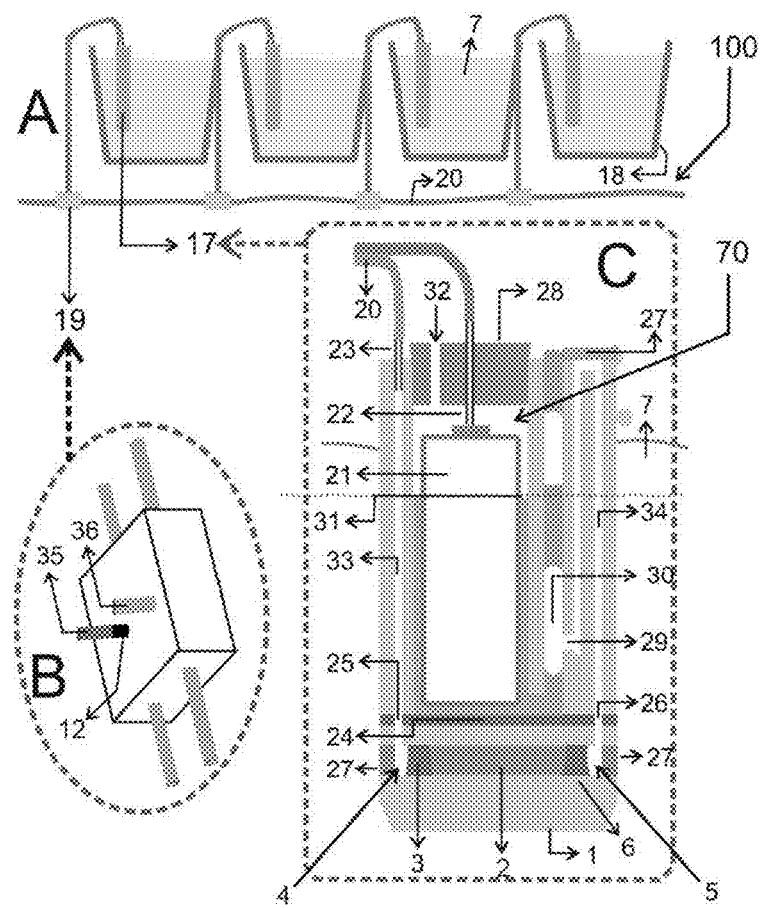
FIG. 6—Irrigation system (100) for propelled watering comprising: A) series fitting of irrigation rods (17), installed in plant vessels (18), fed by twin water and air forks (19) and twin water and air tubes (20); B) twin fork (19) for air circuit (35), through a restrictor (12), and water circuit (36) and C) irrigation rod (17) wherein (1) is the porous support element, (2) non-sintered core, (3) porous blocks, (4) air inflow duct, (5) air outflow duct, (6) water tension sensor in the soil, (7) soil, (21) float, (22) water inflow duct, (23) upper duct, (24) waterproof plate, (25) interfacing element A, (26) interfacing element B, (27) sealing, (28) lid, (29) passage, (30) water outflow duct, (31) water level, (32) air exhaust orifice, (33) air inflow duct, (34) air outflow duct, (70) chamber.

The invention further refers to an irrigation rod (17) shown in FIG. 6 and comprises:
g. a water tension sensor (6) in the soil
h. an air inflow duct (33),
i. an air outflow duct (34),
j. a chamber (70) containing a float (21), a lid (28) endowed with an air exhaust orifice (32) and the water inflow duct (22),
k. a water outflow duct (30) and,
l. a waterproof plate (24).

In said irrigation rod (17), the air inflow duct (33) and the air outflow duct (34) are connected to the ends of the water tension sensor (6) in the soil. A chamber (70) contains irrigation water and is refilled by the water inflow duct (22). The water outflow duct (30) communicates directly with the chamber (70) and indirectly with the air outflow duct (34) by passage (29).

The water tension sensor (6) in the soil, an integral part of the irrigation rod (17) comprises a non-sintered core (2) enveloped by a porous support element (1), said core limited at its ends by porous blocks (3) connected to an air inflow duct (4) and an air outflow duct (5). The non-sintered core (2) of the sensor (6) component of the rod (17) is preferably made of hydrophilic material. More preferably, the hydrophilic material component of the core (2) has a cosine of the contact angle greater than 0.9. Various types of materials can be used to constitute the core (2) of the sensor (6) component of the rod (17) of the invention. Said materials include glass spheres and corundum. The porous support element (1) of the sensor (6) component of the rod (17) is also preferably made of hydrophilic material, said material featuring, also preferably, cosine of the contact angle greater than 0.9. Various materials can be used to constitute the porous support element (1) of the sensor (6) component of the rod (17). Said materials include ceramic, gypsum and pervious concrete. The porous blocks (3) that limit the ends of the sensor (6) component of the rod (17) are preferably made of materials selected from among elastic porous materials and, preferably, hydrophobic.

For the correct operation of the sensor (6) component of the rod (17) of the invention, the porous support element (1) must have, preferably, at least, a bubbling pressure 4 times greater than the critical tension value of the non-sintered core (2).

In a preferred embodiment, said irrigation rod is part of an irrigation system (100) for propelled watering comprising, said system: A) series fitting of irrigation rods (17), installed in plant vessels (18), fed by twin water and air forks (19) and twin water and air tubes (20); B) twin fork (19) for air circuit (35), through a restrictor (12), and water circuit (36).

In another preferred embodiment of the invention, the irrigation system (100) containing the irrigation rod (17) shown in FIG. 6 is a simple way of irrigating a line of vessels (18) using a water pressure regulator having, preferably, 50 kPa of compressed air (10), of a membrane compressor, for example, having output pressure set, preferably, between 3 and 4 kPa, twin tubes (20) of water and air connected along the length, and twin forks (19) of water and air. The engagement of the twin fork (19) and the twin tube (20) facilitates the organization and prevents errors at the time of connecting the irrigation rods (17) in series. In these twin tubes (20) the internal diameters of the water tube is, preferably, twice greater than that of air, for example, 6 mm for the conveyance of water and 3 mm for the conveyance of air, because the viscosity of water is about 10 times higher. The drag rate between the volumes of water and the volumes of air depends on sizing, but for the model described the preferred values are around 0.3 to 0.7 ml of water per ml of air. The twin tubes (20) are coupled on one side of the twin fork at the air circuits (35) and water circuit (36) and on the other side to the upper duct (23) of air passage and to the water overflow tube (22). The twin forks (19), moreover, are practical because they include an air circuit (35) with air flow adjustment restrictors (12).

Inside the irrigation rod the controlled flow of air pushes the water through the water outflow duct (30) and, accordingly, defines the water flow applied, while the soil remains dry and the sensor (6) block the passage of the air flow. In this case the blockage occurs because the intake pressure is reduced, being insufficient to force the passage of the air through the core particles (2), while these contain a sufficient amount of water retained by capillary action in their interstices (equation 1). For the irrigation rod (17) to work correctly, the water level (31) on the inside is kept stable by a float (21) with sealing rubber that is pressed against the water inflow duct (22) obstructing the entry of water. In operation, the water inflow duct (22) is kept fastened on the lid (28), which is endowed with an air exhaust orifice (32).

The air that enters through the upper duct (23), descends through the air inflow duct (33) to the air inflow duct (4), through the core (2) of the sensor (6), flows through the air outflow duct (5), passes through the air outflow duct (34) and traverses the passage (29) to finally enter the tubular water outflow duct (30), which leads the irrigation water, by flotation.

In the water outflow duct (30) the water surface tension is a key component, as it enables the air bubbles introduced into the duct (30) to coalesce, increase in volume and push the water upwards, instead of flowing jointly with the water from the tube in the form of bubbles. This growth behavior of air bubbles in the water outflow duct (30) is consistent and safe for irrigation applications whenever this tubular structure has, preferably, a diameter less than 6 mm and, more preferably, between 2 and 4 mm.

The seal (27) for closing openings in the irrigation rod (17) facilitates the preparation of ceramic pieces in perforated molds. The waterproof plate (24) can also be manufactured in injected thermoplastic and must have interfacing element A (25) and interfacing element B (26) to drive the air.

In a preferred embodiment for domestic environments, the restrictors (12) adjust the air flow at 3 kPa between 0.5 and 5 ml/min for watering vessels (18). In another preferred embodiment of application for arboreal plants this air flow through the restrictor (12) has a greater order of magnitude. The elongated irrigation rods (17) of the present invention contain significant improvements in relation to state of the art documents. The improvements refer to greater simplicity in the distribution of pipes, twin forks (19), twin tubes (20), and sensor (6) that allows the irrigation rod (17) to be fastened and driven directly.

In another preferred embodiment of the invention, the irrigation rod has about 150 mm in height and diameter of about 35 mm being easily buried in the substrate of the vessel (18) or in the soil. Optionally, an L-shaped tube can be coupled out at the level of the top of the water outflow duct (30), if it is desirable to position the dripping at the side of the core sensor (6). Optionally, the length of the irrigation rod can be increased by extending the thickness of the waterproof plate (24).

In the case of the irrigation system (100) for propelled watering, the series fitting of the irrigation rods (17) is done with simplicity by using the twin forks (19) (FIG. 6) to connect, without the possibility of error, twin tubes (20) that separately convey the air and the water. These extruded tubes are preferably black to prevent the growth of algae. Typically, a miniature air compressor with a flow of 4 liters per minute, enables the application of over 1000 liters of water per day, which is sufficient for most domestic applications.

The sensor (6) of the present invention is simple and can be prepared to meet various agronomical demands, starting with modest water tensions from 2 to 10 kPa for substrates of vessels (18), passing through intermediary values between 15 and 40 kPa for applications in horticulture and reaching high values of up to at least 200 kPa for applications in fruticulture and in cereal production.

In applications for water irrigation management of substrates with low capacity to retain water, technically demanded for use in vessels and for seedlings, it is recommended that the critical tension of water or bubbling pressure (Pb) of the core (2) in water in equation 1 be defined with values between 5 and 12 kPa, whereas for field management this critical tension Pb may be, in most applications, between 10 and 50 kPa. Sensors (6) with greater water tensions, for example, over 200 kPa, may be used and, chiefly, for water deficit tolerant crops and for cultivation conditions that require the application of controlled irrigation deficit, in specific development stages of the crop.

Figure 7:
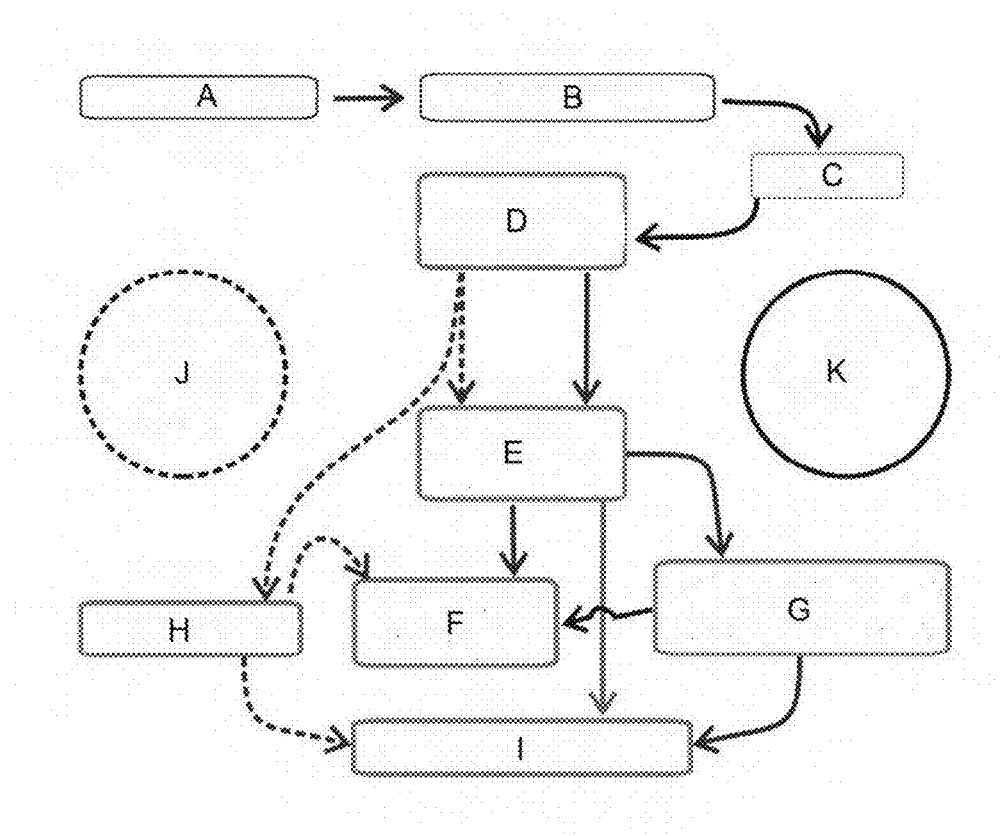
FIG. 7: Black diagram illustrating the possibilities of use of the water tension sensor (6) wherein (A) is the compressed air, (B) pressure setting, (C) restrictor, (D) water tension sensor, (E) pressure transducer, (F) irrigation management, (G) reading of the soil-water, (H) air exhaust, (I) automatic irrigation, (J) intermittent air exhaust, (K) continuous air exhaust.

Irrigation management applications can be effectively implemented with the sensor (6), both with manual procedures as with automated procedures, as illustrated in the block diagram of FIG. 7, which summarizes the different possible automatic or manual procedures with the use of the sensor (6). In FIG. 7, the possibilities of using the water tension sensor (6) involve the use of (A) compressed air, (B) pressure setting, (C) restrictor, (D) water tension sensor, (E) pressure transducer, (F) irrigation management, (G) soil-water reading, (H) air exhaust, (I) automatic irrigation, (J) intermittent air exhaust, and (K) being continuous air exhaust.

With automation, the depressurization at the entry of the core sensor (6), may, for example, be detected in a pressure switch which drives the irrigation by way of a solenoid valve. A timer may complement the system to keep irrigation for sufficient time to moisten the whole root system. Alternatively, irrigation is simply switched off when there is an increase in pressure in the sensor (6) due to the moistening of the soil after irrigation. Irrigation technicians generally consider the timed procedure as best, as it assures infiltration of the water to the entire effective depth of the root system. The manual method of irrigation management, being less costly, can also be executed with the system (80) for characterization and continuous soil-water readings constructed with a sensor (6), as shown in FIG. 2A, or with even fewer costs by employing critical irrigation tension indicators, as shown in FIGS. 5A and 5B.

Both control with manual monitoring, as with automated data acquisition, enable correct irrigation management. In particular, automatic management can be performed simply by using the system (80) for characterization and continuous soil-water readings (FIG. 2A) and an electronic system for automatic data collection (water tension in the soil determined by equation 1).

The water tension sensor (6) in the soil designed for management and control of irrigation water of this invention, pneumatically operated, may additionally have electrical outputs by simply adding a lamp (47) and a light sensor (48) to measure the variation of the water tension in the soil according to the variation of the light reflection that interacts with the water on the non-sintered core particles (2).

Thus, the present invention additionally comprises a soil-water sensor (110) with light reflection reading on the non-sintered core (2). Said sensor (110) comprises a porous support element (1) and water conduction by capitally action between the soil (7) and the core (2) of non-sintered particles, cover (46), lamp (47) and light sensor (48). In this arrangement, the porous support element (1) provides hydraulic contact between the soil (7) and the non-sintered core particles (2), by capillary action. In the cover (46) with a lamp (47), a light sensor (48) enables a reading of the variations of intensity of the light reflected on the water and on the core particles (2) based on the water tension in the soil. In said sensor (110) of the invention, the response curve to the soil-water is altered based on the dimension and on the shape of the non-sintered core particles (2). Said core particles (2) are aggregated together and to the porous element (1). Further, in said sensor (110), the response generated from soil-water (7) depends on the micrometric hydrophilic textures recorded on the core (2). The response generated from soil-water (7) also is influenced by the surface textures recorded directly on the internal surface of the porous element (1).

As in the other applications of this invention described previously, higher measurement values of water tensions require the use of particles with a smaller diameter (eq. 2 and 3). For the use of the light reflection method, the core particles (2) should preferably be regular and spherical. Spheres of transparent and also opaque materials, including black colored, can be used in this application. Preferably glass spheres are used, as they are easily obtainable. In a preferred embodiment of the invention, transparent glass spheres with a diameter of between 40 and 100 micrometers are used.

The present invention also refers to a sensor (120) having non-sintered core to measure soil-water by light transmission comprising a porous support element (1) and hydraulic contact between the soil (7) and the non-sintered core (2) arranged as a laminar aggregate, cover (46) for fastening the lamp (47) on the one side and the light sensor (48) on the other. In said sensor (120), the response curve to the water tension depends on the thickness of the core (2) and of the dimensions of their particles. Preferably, said particles should be spherical and transparent.

For the use of the light transmission method, the core particles (2) should preferably be regular and spherical. Spheres of transparent and also opaque materials, including black colored, can be used in this application Preferably glass spheres are used, as they are easily obtainable. In a preferred embodiment of the invention, transparent glass spheres with a diameter of between 40 and 100 micrometers are used.

Figure 8:
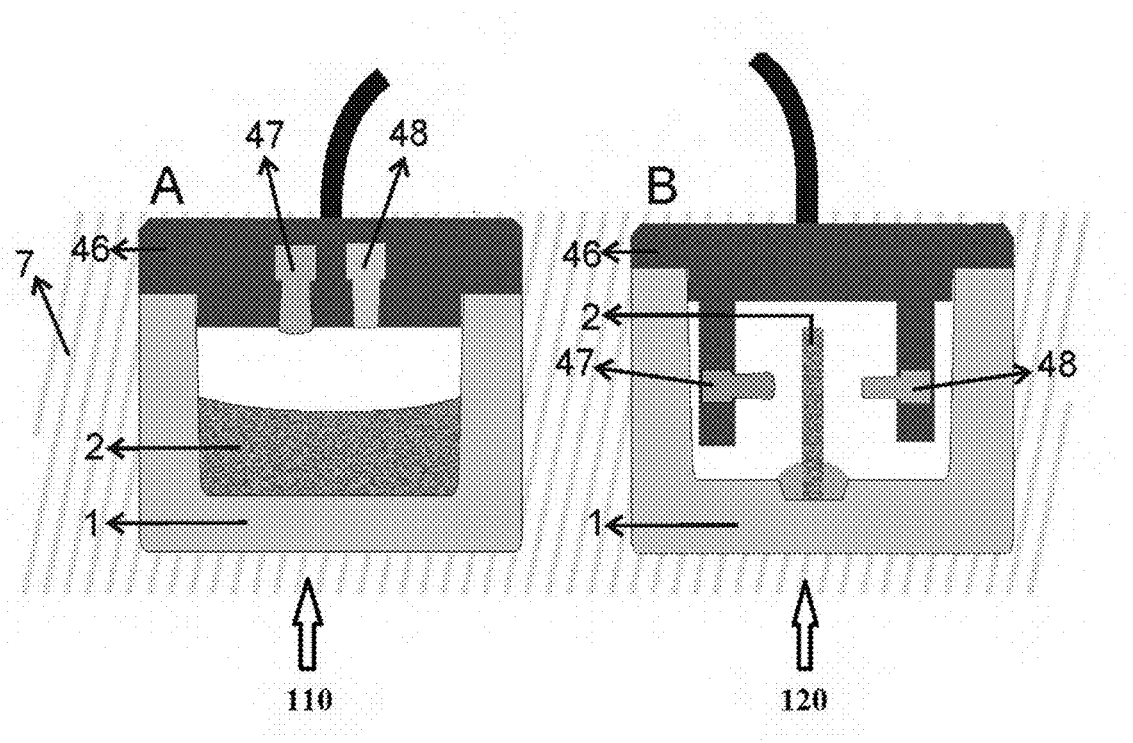
FIG. 8: Soil-water sensors for reading by reflection and by light transmission, according to electrical current readings. A) Sensor (110) for reading by light reflection made of a porous support element (1) to promote hydraulic contact by capillary action between the soil (7) and the non-sintered core (2), cover (46), lamp (47) and light sensor (48). B) Sensor (120) for light transmission reading made of a porous support element (1) to promote hydraulic contact by capillary action between the soil (7) and the core (2) prepared in lamellar form by aggregating glass spheres or other transparent granular material, lamp (47) and light sensor (48).

In the water tension sensor (120) shown in FIG. 8B, a reading is used by light transmission through a non-sintered core (2) preferably laminar. This laminar core (2) of glass spheres linked by an adhesive, or binder, as in the other applications of this invention provides for the conveyance of water between the soil (7) and the core (2) by capillary action. In the system, lighting is applied by lamp (47), for example de LED (light-emitting diode) and a reading is made with light sensor (48), for example, by electrical current generated in a photodiode.

In a preferred embodiment of the invention, said soil-water sensor (120) by light transmission comprises transparent plates to contain the core particles (2). In this case, said core particles (2) are preferably in laminated arrangement without the need for using a binder element. For preparing soil-water sensors by reflection (110) and by transmission (120) of the invention, the relationship between the bubbling pressure and the diameter of the glass spheres used facilitates the process of obtaining sensors with response to the expected water tension. Consequently, it is valuable to know that the capillary rise, or bubbling pressure (pB) of air in meters, at 20 degrees Celsius, for water between glass spheres of the core (2) can be approximated with the aid of the expression:

$$pB \sim 16\ \sigma/\rho g D 15 D 0.000115 \sim /D \qquad \text{eq. 2}$$

Wherein $\sigma$ is the surface tension of the water (0.0278 N/m a 20 Celsius), $\rho$ is the specific weight of the water (~1000 kgf/m3), g is an acceleration of gravity at the Earth's surface (~9.81 m/s$^2$) and D is the diameter of the glass spheres (m). These approximate results of bubbling pressure in meters of water column may, in sequence, be converted to values in kPa, multiplying them by ten.

In the sensors soil-water by reflection (110) and by transmission (120) of the invention, the electric signal of light reflection generated based on the soil-water (7) depends on the curvature radius (r) of the menisci water/air over the core particles (2). This curvature radius in turn is a function of the water tension (T) and can be approximated by water retention in capillary tubes of the type given in equation 3.

$$T = 2\sigma/(\rho g r) \qquad \text{eq. 3}$$

As an additional simplification, the cosine of the contact angle was approximately the value 1.0 and accordingly was not included in equation 3. Under these approaches, it can be inferred that the water tension influences the surface texture of the menisci and, consequently, the light reflections patterns according to a simple relationship with the water tension in the soil.

Water tension sensors by light reflection of the invention, with porous cores (2), sintered or otherwise, according to equations 2 and 3 may additionally be prepared by adding support textures for the water/air menisci, whose radius is a function similar to equation 3. Designated thus, these sensors may also have the surface of the core (2) recorded by compression against a rigid plate of glass, for example, containing embossed micrometric texture patters. These patterns are a useful alternative for obtaining reading sensitivity under reduced water tensions. Another application of this type of construction is to make miniature and thus quick-responding sensors that are easily aggregated to complex systems that require various types of sensors, such as, for example, electrical conductivity and temperature.

Installing the pneumatic or electric core sensors (2), described in the present invention, in the soil to monitor the water tension in the soil between the plant roots requires the following care:

a) Dig the soil and install the sensor between the roots, and, usually, to half the effective depth of the roots, when it is desirable to determine the time for irrigation;

b) Add soil by squeezing it with the care of leaving it compacted similar to the original.

If the sensor (6) has a non-sintered core (2) with loose particles, that is, prepared without the use of any binder, then the following additional care is necessary in installing the sensor in the soil:

c) Air-dry the sensor until it achieves the dry reference weight and;

d) In the pit, place the sensor in a horizontal position before adding soil.

The applications of the sensors described in the present invention for controlling irrigation and for measuring soil-water in general are started after applying an initial watering.

To form the non-sintered core as an aggregate of glass spheres, an adhesive or a binder can be used. As a transparent paint binder having sodium silicate as base and UV resins are simple alternatives, especially when the glass spheres are designed to measure water tensions lower than 20 kPa.

The core sensors (120) having light transmission reading also can be prepared with non-sintered loose particles in the non-sintered core (2). In this case the reading is made possible by fastening transparent glass plates on the side which retain a laminar layer of glass spheres in contact with the porous element (1). However, this method is less sensitive, given the alterations that the glass plates introduce into the system.

The laminar unit can be prepared with the aid of transparent plastic plates, separated by spacers laterally to admit few layers of glass spheres. The upper plate is removed and the sodium silicate-based binder is added. After curing the plate-shaped core (2), it is fastened to the porous element with the aid of gypsum or pervious concrete.

The use of fewer layers of glass spheres, for light transmission measurements, is important because light refractive indices of the components of the porous medium that influence the reflection and transmission of light are substantially different from each other and have approximate magnitudes of 1.50 for glass, 1.00 for air and 1.33 for water. Glass has a greater light refraction index and substantially different to water refraction index and accordingly causes substantial dispersion and absorption of light, which may adversely affect the sensitivity to the water tension by light transmission insofar as it increases the number of layers of glass spheres. The water that is retained by capillary action between the spheres frustrates the total reflection of light, which occurs in greater quantity as soil dries. Thus there is a decrease in the transmission of light through the laminated core (2) (FIG. 8B) when the water tension increases and the spaces between the glass spheres are progressively occupied by air. In this system in particular, it is important to note that the light transmission response also comprises a component that increases the light dispersion based on the increase in water tension, caused by reflection.

When the spheres are made of material with a higher refraction index than glass, the reflection in the surface layers dominates the response obtained. In contrast, for light transmission applications, ideally the glass spheres should have a refraction index closer to that of water, so that the effect of the transmission in the saturated sensor is nearer to that of transmission from pure water.

Figure 9:
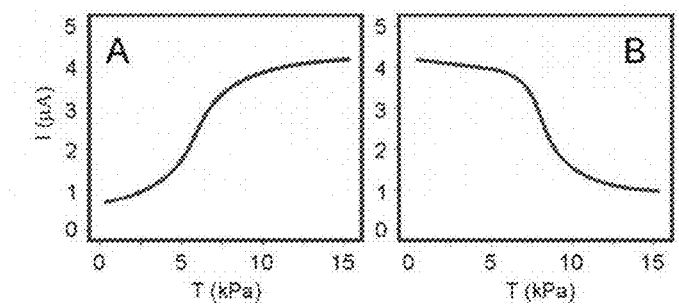
FIG. 9: Typical response to soil-water (T) of the water tension sensors for reading by reflection and by light transmission, measured in terms of electrical current. 9A) Curve of light reflection in sensor (110) based on the water tension in the soil. 9B) Light transmission in a sensor (120) based on the water tension in the soil. The core (2) in these sensors (6) was formed using transparent glass spheres with a diameter between 40 and 100 micrometers.

FIG. 9B illustrates the variation of light transmission, expressed as electrical current, from a photodiode type light sensor (48), based on the increase of water tension in the soil (7), for the sensor (120) illustrated in FIG. 8B. It is noted that the reduction of light transmission, which passes between the spheres retaining water by capillary action is of the sigmoid type. The sigmoid curves of FIGS. 9A and 9B enable simple electrical control of irrigation water, with the aid of industrial controllers sensitive to electrical current that automatically trigger solenoid valves at specified soil-water values. With these water tension curves versus electrical current, it is also possible to estimate the water tension in the soil at each instant based on the electrical current values obtained.

The sensor (6) having a non-sintered core (2) (FIG. 1) is ideal for manufacturing different types of automatic irrigation rods that water by pneumatic mechanisms, based on the water tension in the soil. These automated pneumatic irrigation systems can also operate without the use of compressed air (10) and pressure setting, as illustrated in FIG. 6. Systems of automatic irrigation rods that use pressurization measured by mechanisms such as heating in solar collectors (67) and pressurization induced by a hanging water column retained by partial vacuum inside a tensioning tube (78) are simpler to use, because they feature internal gas compression mechanisms for driving the automation, which substitute the external use of compressed air (10). These systems can be visualized in FIG. 10 (solar collector) and 14 (hanging water column).

Figure 11:
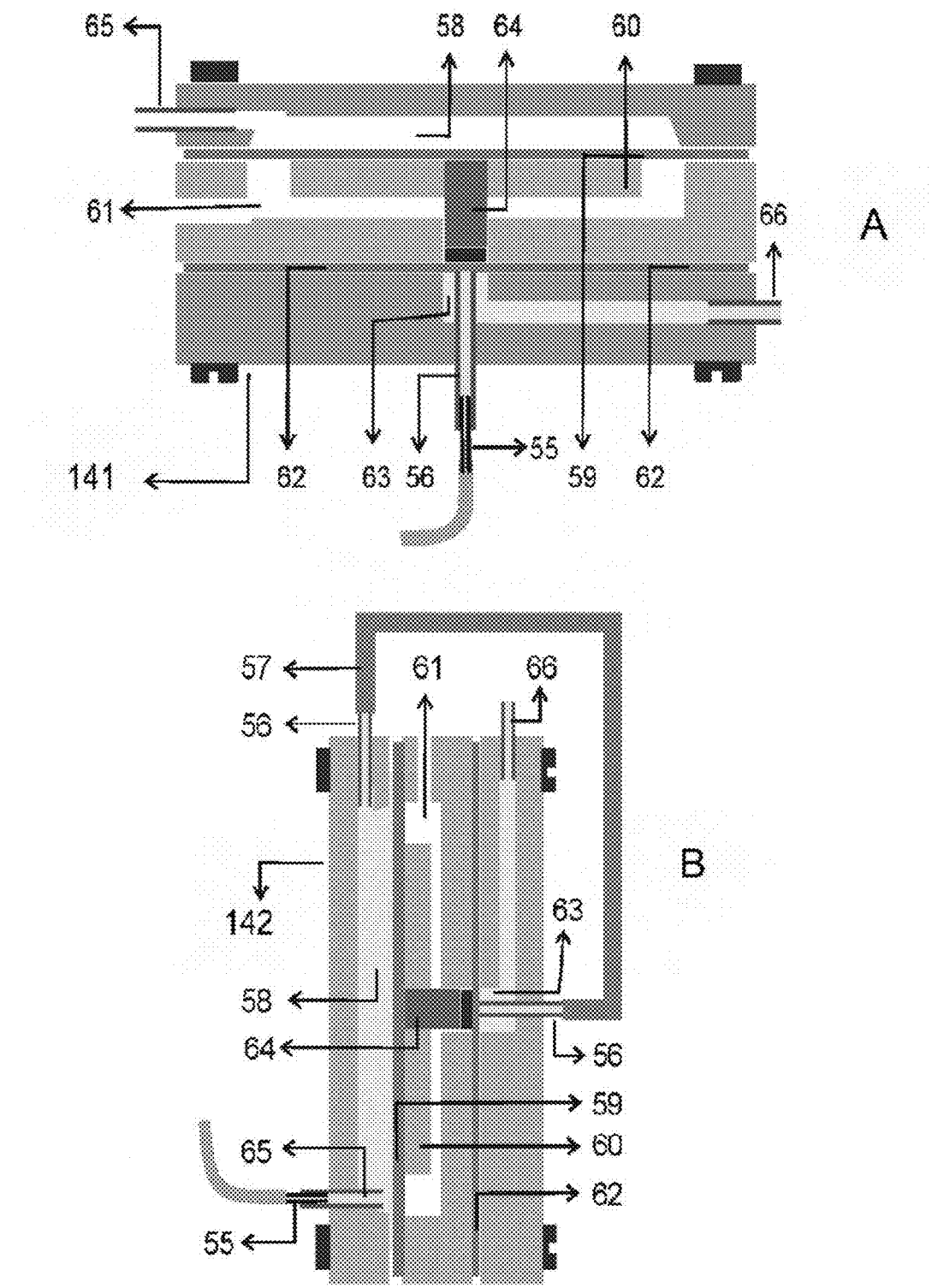
FIG. 11: A—Differential pressure valve (141) for controlling the flow of fluids coming from the water mains pipe comprising inflow duct (66), tubular water flow restrictor (55), lower chamber (63), middle chamber (61), closing diaphragm (62), side chamber (58), middle chamber (61), clamping diaphragm (59), disc (60), pin (64), overflow duct (56), tightening screws and fittings (65), B— Pressure divider (142) for controlling the flow of fluids coming from the water mains pipe comprising overflow duct (56), tube (57), fitting (65), side chamber (58), clamping diaphragm (59), closing diaphragm (62), tubular water flow restrictor (55).

In these automatic irrigation rods, the control mediated by the pneumatic sensor (6) can be made with flow control valves having pressure setting or detection, among which two particularly useful arrangements are illustrated in FIGS. 11A and 11B.

In this context, the invention additionally refers to an irrigation rod (140) having automated thermal pressurization with a pneumatic soil-water sensor comprising:
  inflow duct (66);
  differential pressure valve (141);
  core sensor (6) installed in the soil (7);
  air inflow duct (4);
  solar collector (67);
  high fitting (51);
  middle chamber (61);
  pressure relief in the middle chamber (61),
  air flow restrictor (12);
  pin (64) between the clamping diaphragm (59);
  closing diaphragm (62);
  disc (60);
  overflow duct (56),
  raised irrigation duct (68);
  water flow restrictor 143);
  fitting (65) of the side chamber (58); and
  foot (79) for fastening the irrigation rod to the ground.

Preferably, said irrigation rod (140) having automated thermal pressurization with a pneumatic soil-water sensor has an inflow duct located in the differential pressure valve (141). Also preferably, the core sensor (6) installed in the soil (7) is linked on one side by the air inflow duct (4) to the solar collector (67) and on the other side to the high fitting (51) to the middle chamber (61). More preferably, the pressure relief in the middle chamber (61) of said rod (140) is by way of the air flow restrictor (12). In a preferred embodiment of the rod (140) of the invention, the pin (64) is located between the clamping diaphragm (59) and the closing diaphragm (62). In another preferred embodiment of the rod (140) of the invention, a fitting (65) is open to the atmosphere.

Figure 10:
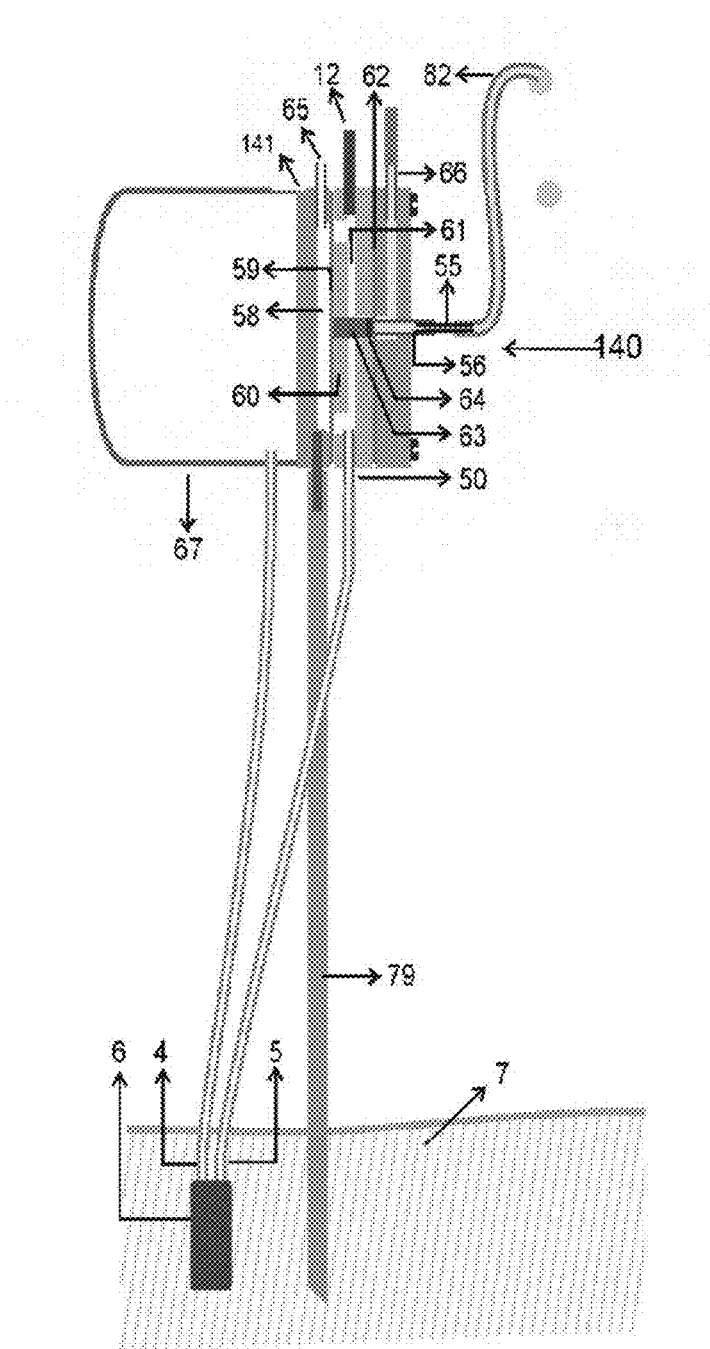
FIG. 10: Irrigation rod with automated thermal pressurization with a pneumatic soil-water sensor comprising an inflow duct (66), tubular water flow restrictor (55), solar collector (67), middle chamber (61), clamping diaphragm (59), pin (64) overflow duct (56), closing diaphragm (62), raised irrigation duct (68), side chamber (58), fitting (65), air flow restrictor (12), and foot (79).

In the thermal automation irrigation rod (140) illustrated in FIG. 10, a differential pressure valve (141) is preferably used, similar to the one illustrated in FIG. 11A, which is fed by way of the inflow duct (66) and has a side chamber (58) open to the atmosphere. In dry soil, over a critical water tension, the sensor (6) opens for the passage of air between the air inflow duct (4) and the air outflow duct (5). In this condition, exposure of the solar collector (67) to increased radiation intensity causes heating and increased air pressure, which is communicated by way of the sensor (6) to the middle chamber (61) where irrigation is produced through the raised irrigation duct (68). The heating by pressurizing the middle chamber (61) and reducing the force on the pin (64) enables the water to flow under the closing diaphragm (62) with sufficient pressure for watering by way of the raised irrigation duct (68).

In the middle chamber (61) there is a slow reduction of pressure governed by an air flow restrictor (12), which is specified so that in half depressurization time assays, under constant temperature, an applied pressure increase of 20 kPa is reduced to 10 kPa in a time interval of between 0.25 and 2 hours. This provision assures that the watering is interrupted in a few minutes after the wetting front has moistened the sensor (6). The side chamber (58) is kept open to the atmosphere through the fitting (65). In moist soil, the sensor closes the passage of air and thermal pressurization is dissipated by way of the air flow restrictor (12), cause the increased force applied by the clamping diaphragm (59) interrupts watering by action of the closing diaphragm (62) on the overflow duct (56).

The system as specified does not activate irrigation during periods of stable temperature, since the water pressure by way of the raised irrigation duct (68) acts on the side chamber (58) producing on the clamping diaphragm (59) a sufficient force for the pin (64) to close the passage of water, by its action on the closing diaphragm (62) in the lower chamber (63), obstructing the overflow of water by being tightened on the entry of the overflow duct (56).

The thermal automation irrigation rod system (140) illustrated in FIG. 10 is robust and is didactically and educationally appealing because it causes irrigation, associated to the fluctuation of the radiation intensity of the sun on the solar collector (67). It is therefore a valuable system for watering plants in ambience applications, integrated to agricultural and ecological scenarios.

In a preferred embodiment of the rod (140) of the invention, a practical and simple valve (141) is used for automation applications (illustrated in FIG. 11A). In the differential pressure valve (141) arrangement with three chambers, the water mains pipe is linked to the inflow duct (66) and the water flows from the lower chamber (63) through the tubular water flow restrictor (55). The middle chamber (61), in turn, is separated from the lower chamber (63) by the closing diaphragm (62) and of the side chamber (58) by the clamping diaphragm (59). A disc (60) reinforces the clamping diaphragm (59) and is used to fasten the pin (64). Sized according to the application, the area of the clamping diaphragm is typically specified with a value of 5 to 200 times greater than the flexible area of the closing diaphragm (62), which is tightened by the pin (64) for closing the passage of water by way of the overflow duct (56). The flow of water in the differential valve (141) is limited by a tubular water flow restrictor (55), placed after the overflow duct (56). Tightening screws and one or more fittings (65) opening to the atmosphere, affixed to the side chamber (58) complement the valve.

With simple modifications, the differential pressure valve (141) can perform different functions, including that of acting as a pressure divider (142) relative to the pressure entering the lower chamber (63) (FIG. 11B). The pressure division is obtained by connecting the overflow duct (56) to the fitting (65) of the side chamber (58) by means of the tube (57). With the middle chamber (61) open to the atmosphere, the divided pressure is established on the side chamber (58). Based on this divided pressure, it is possible, for example, to derive a regulated flow of water from an additional fitting (65).

The present invention also comprises a molded restrictor (143) with water flow resistant to the increase in pressure and with cleaning by backwashing comprising:
water inflow duct (66);
opening (75)
closing diaphragm (62),
flow setting channel (71);
compression channel (74); and
support grooves (70).

Figure 12:
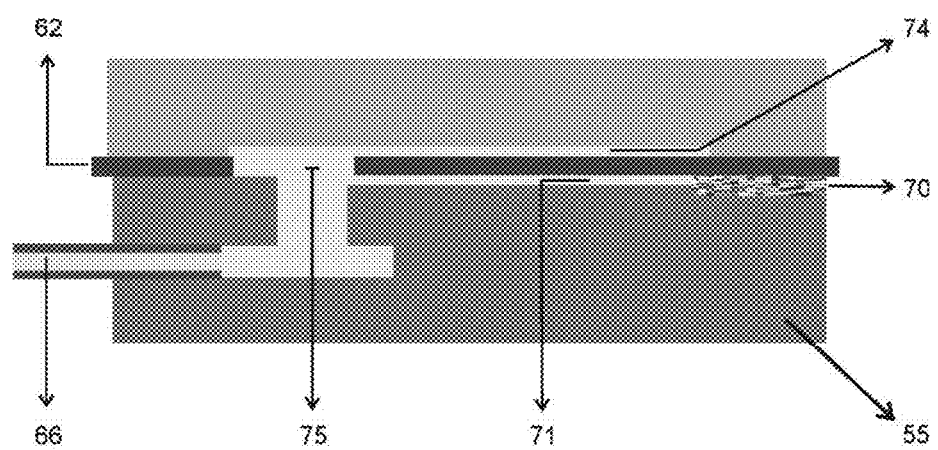
FIG. 12: Detail of a molded restrictor (143) for water flow fed via the water inflow duct (66), comprising opening (75), closing diaphragm (62), flow setting channel (71), compression channel (74), support grooves (70), closing diaphragm (62), lower chamber (63).

FIG. 12 illustrates a detail of the molded restrictor (143) of the invention for easy construction of water flow by plastic injection procedures, since it involves just one flow setting channel (71), one compression channel (74) and support grooves (70). The support grooves (70) are deeper than they are wide and should preferably have a width less than half the thickness of the closing diaphragm (62). Thus, if the closing diaphragm (62) is one polybutene membrane 0.6 mm thick, the support grooves (70) should have a maximum width of 0.3 mm. Therefore, the water flows towards the lower chamber (63) while the closing diaphragm (62) interrupts the passage of water entering through the opening (75), and pressurizes the route between the compression channel (74) and the lower chamber (63).

In this full arrangement, a molded restrictor (143) with response hardly dependent on the water pressure, in the range of 30 to 300 kPa. Additionally, the compression channel (74) makes the molded restrictor (143) suited for cleaning by backwashing, since the flow by backwashing is various times greater than in the working direction. Losing the insensitivity to pressure, the molded restrictor (143) for water flow (can be made in a simplified manner by subtracting components. In an extreme situation, just one flow setting channel (71) can be left under the closing diaphragm (62). In this simplified version, a very simple molded water flow restrictor (143) is obtained, but one which has problems relating to presenting the proportional flow to the water pressure applied and is sensitive when tightening on the closing diaphragm (62), established in the manufacture. Another possible simplification, if the flow setting channel (71) is wider than twice the thickness of the membrane, is to omit the compression channel (74) since for the effectiveness of the molded water flow restrictor (143), the water moves efficiently between that channel and the neighboring upper layer of the closing diaphragm (62). This omission, however, adversely affects the susceptibility of the molded water flow restrictor (143) in backwashing.

This molded restrictor (143) for water flow shown in FIG. 12 has self-cleaning features and enables the use of simpler water filtration systems, with less loss of load and lower cost. In most practical applications, the water flow through the restriction is adjusted between to values between 200 ml and 4.000 ml per hour.

The present invention further comprises a water irrigation rod (150) with adjustable angle duct comprising:
pressure divider (142);
angle duct (76);
inflow duct (66);
lower chamber (63)
molded restrictor (143) for water flow; lower chamber (63);
middle chamber (61);
closing diaphragm (62); side chamber (58);
middle chamber (61);
clamping diaphragm (59);
disc (60),
pin (64);
overflow duct (56);
fitting (65); and
foot (79) for fastening the irrigation rod to the ground.

Preferably, the inflow duct (66) of said rod (150) is linked to the lower chamber (63) through a molded restrictor (143) for water flow. Also preferably, the lower chamber (63) is separated from the middle chamber (61) by the closing diaphragm (62). In a preferred embodiment of the rod (150) of the invention, the side chamber is separated from the middle chamber (61) by the clamping diaphragm (59). In another preferred embodiment of the rod (150) of the invention, the disc (60) houses the pin (64).

Figure 13:
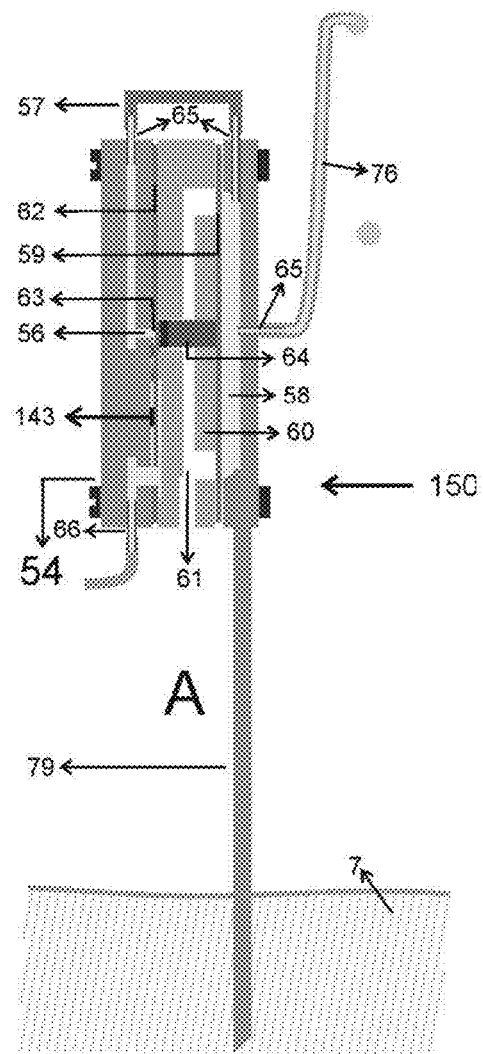
FIG. 13: Non-automatic, settable irrigation rod (150) with use of the pressure divider (142) as irrigation rod with modulation of the water flow in an angle duct (76), wherein the water column adjusts and, consequently, the pressure that regulates the water flow for watering.

In the rod (150) of the present invention shown in FIG. 13, the pressure divider (142) is used as a non-automatic irrigation rod, with a flow defined through the molded restrictor (143) for water flow. If the ratio between the area of the clamping diaphragm (59) and the area of the closing diaphragm (62) is equal to 100, for example, an adduction pressure of 50 kPa is reduced to about 0.5 kPa. Thanks to this pressure division with an irrigation rod (150), the water flow can be adjusted, non-automatically, by varying the position of the angle duct (76), with which the height of a water column is regulated and, therefore, the pressure that determines the water flow applied in the watering. Accordingly, it is possible to adjust the angle duct (76) to flow between zero, adjusting it near to the top, and a maximum flow, with angle duct (76) adjusted at minimum position, that is, at the base.

With minor modifications, the irrigation rod (150) of the invention enables an automatic irrigation rod to be manufactured. Accordingly, the present invention also refers to an automatic irrigation rod (160) with pressurization by a hanging water column controlled by pneumatic soil-water sensor comprising:
- inflow duct (66);
- lower chamber (63),
- molded water flow restrictor (143);
- sensor (6) with air inflow duct (4) and air outflow duct;
- high fitting (51),
- middle chamber (61),
- differential pressure valve (141);
- overflow duct (56);
- side chamber (58);
- clamping diaphragm (59);
- disc (60);
- closing diaphragm (62);
- pin (64);
- tensioning tube (78); and
- foot (79) for fastening the irrigation rod to the ground.

Preferably, the inflow duct (66) of the rod (160) of the invention is linked to the lower chamber (63) by way of a tubular water flow restrictor (55). Also preferably, the air outflow duct (5) of the sensor (6) is linked to the high fitting (51) in the differential pressure valve (141). In a preferred embodiment of the rod (160) of the invention, the overflow duct (56) output of the lower chamber (63) is linked to the middle chamber (61). In another preferred embodiment of the rod (160) of the invention, the side chamber (58) is separated from the middle chamber (61) by the clamping diaphragm (59). More preferably, the lower chamber (63) of the rod (160) of the invention is separated from the middle chamber (61) by the closing diaphragm (62). Also preferably, the rod (160) of the invention comprises an opening (77) between the lower chamber (63) and the middle chamber (61).

Figure 14:
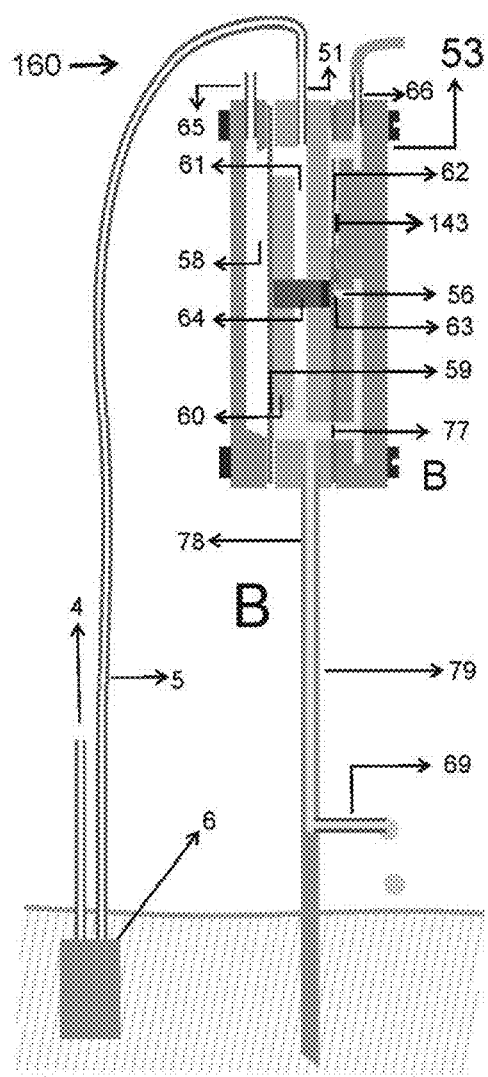
FIG. 14: Automatic irrigation rod (160) of hanging water column for the pressurized automatic watering by water column and controlled by a pneumatic soil-water sensor (6) and comprising an inflow duct (66), air outflow duct (5), high fitting (51), middle chamber (61), differential pressure valve (141), air inflow duct (4), molded water flow restrictor (143), lower chamber (63), clamping diaphragm (59), disc (60), closing diaphragm (62), pin (64), overflow duct (56), fitting (65), side chamber (58), lower chamber (63), opening (77), tensioning tube (78), side runoff (69) and fastening foot (79).

In said rod (160) of the invention, the sensor (6) having non-sintered core (2) opens the passage of air between the air inflow duct (4) and the air outflow duct (5) (12B), when the soil dries and exceeds a critical water tension value, which is a function of the size of the particles employed to fill the non-sintered core (2) of the sensor (6). For this application, a differential pressure valve (141) can be used to automate the irrigation following the scheme illustrated in FIG. 14. In this automatic water column irrigation rod (160), the air outflow duct (5) of the sensor (6) is hermetically linked to the middle chamber (61) by the high fitting (51). This assures that the water does not drain by gravity towards the sensor (6). The air inflow duct (4) of the sensor (6), on the other hand, is kept outside the soil (7) with a view to preventing suction and drag and soil particles inside the sensor (6) once irrigation is interrupted.

Power for the automatic irrigation rod pressurized by hanging water column is provided by way of the inflow duct (66) and the molded water flow restrictor (143). The water flows, under the closing diaphragm (62), to the overflow duct (56) whenever the force applied by the pin (64) in the lower chamber (63) is insufficient to block the passage of water. The overflow duct (56), in turn, conveys water to the lower part of the middle chamber (61), through the opening (77), from where the water descends through the tensioning tube (78), and flows through the opening of the side runoff (69).

To produce the partial vacuum needed to close the irrigation, the vertical tensioning tube (78) must have a length to produce sufficient partial vacuum such that the clamping diaphragm (59), reinforced by a disc (60), closes the flow of water whenever the product of the partial vacuum in the middle chamber (61) times the area of the clamping diaphragm (59) becomes greater than the product between the entry pressure times the flexionable area under the pin (64) in the closing diaphragm (62). In these operations, the fitting (65) of the side chamber (58) is kept open. The miniature automatic irrigation rod of FIG. 14 can be fastened to the soil or on a plant vessel by a foot (79), which can be the extension of the tensioning tube (78) itself, through where there may optionally be a water output by way of side runoff (69).

The tensioning tube (78) must preferably have an inner diameter in the range of 2 mm to 4 mm. Larger diameters may cause air to enter through the control tube end and, consequently, water flow out that is not automatically controlled by the passage of air between the ducts (4 and 5) of the sensor (6) in dry soil conditions. With smaller diameters, the very surface tension of the water may paralyze irrigation. The water flow that traverses the molded water flow restrictor (143) must be always less than a threshold value, for example 1 liter per hour, depending on the diameter and the length of the tensioning tube (78), so that no positive pressure induction occurs, causing the rising of water to the top of the high fitting (51), to the point of causing overflow into the inside of the sensor (6). Additionally, in the handing column irrigation rod the high fitting (51) must be at least 5 cm high so that the surface tension at the entry of the tensioning tube (78) does not raise the water level, at the start of watering, to the point of causing water to flow over into the inside of the sensor (6).

In the automatic irrigation rod (160) pressurized by water column (FIG. 14) (partial vacuum), irrigation closes when the tensioning tube (78), rigid and vertical, at the base of the middle chamber (61), has a sufficiently long water column due to the blockage of the air flow through the sensor (6). Thus, it produces a partial vacuum (pressurization) in the middle chamber (61) sufficient to shut the flow of water through a force that induces the clamping diaphragm (59) through the pin (64) on the closing diaphragm (62) and the overflow tube (56).

The sensor (6) having non-sintered core (2) of the invention is ideal for driving the automatic irrigation rod pressurized by water column (FIG. 14), whose pressurization is of the partial vacuum type. This capacity to operate under partial vacuum, without suffering loss of performance, is a quality deriving from the fact that the outer porous element (1) of the sensor filters all the water coming into the non-sintered core (2). In this sense, maintaining the air inflow duct (4) outside of the soil assists in preventing the suction of particles of the soil to the inside of the non-sintered core (2), where they might cause loss of performance of the sensor by increasing the water tension necessary for triggering irrigation. The thermal pressurization irrigation rod (140), on the other hand, is peculiar, because although it waters when the pressure in the solar collector (67) increases, it also exposes the sensor (6) to negative pressure periods in cooler hours. The thermal pressurization irrigation rod (140) (FIG. 10) requires, therefore, all the essential features of the sensor (6), including an internal passage of air between the air inflow duct (4) and air outflow duct (5)

As main advantage, the automatic irrigation rod (160) pressurized by hanging water column (FIG. 14) is simpler and miniaturizable among all the automatic irrigation rods shown in this document.

The present invention further comprises a dual pneumatic soil-water sensor (180) with aggregate response through an air inflow duct and an air outflow duct comprising:
outer porous element (1);
upper sensor (72);
lower sensor (73);
non-sintered core (2);
air inflow duct (4);
porous block (3);
air outflow duct (5)

Preferably, in said sensor (180) of the invention, the non-sintered core (2) is made of glass spheres or corundum. Also preferably, the air inflow duct (4) is common to the upper sensor (72) and lower sensor (73). In a preferred embodiment of the sensor (180) of the invention, the air outflow duct (5) links the upper sensor (72) to the lower sensor (73).

To maintain the profile of the soil properly irrigated along the effective depth of the roots facilitates water absorption by plants and the essential mineral elements retained in the soil. Thus, the use of the dual-depth sensor (180) of the invention is one of the alternatives for monitoring and controlling the watering so as to assure that the profile of the soil exploited by the roots is kept always with water tension or humidity within the technical specified ranges, except for the surface layers which dry very quickly.

Elongated tubular body sensors, low cost and easy to install in the soil, sensitive to water tension or humidity of the soil, at different (multiple) depths and which contain a simple output for automatic irrigation control systems are still an unmet demand by the irrigation industry. In this sense, the use of the non-sintered core (2) facilitates the preparation of dual sensors, that is, sensitive at two depths, and mounted on a single body of tubular porous element (1), as illustrated in FIG. 12. These dual tubular sensors (180) are more easily prepared for pneumatic operation. They are useful for driving automatic irrigation systems such as those illustrated in FIGS. 10, 13 and 14.

Figure 15:
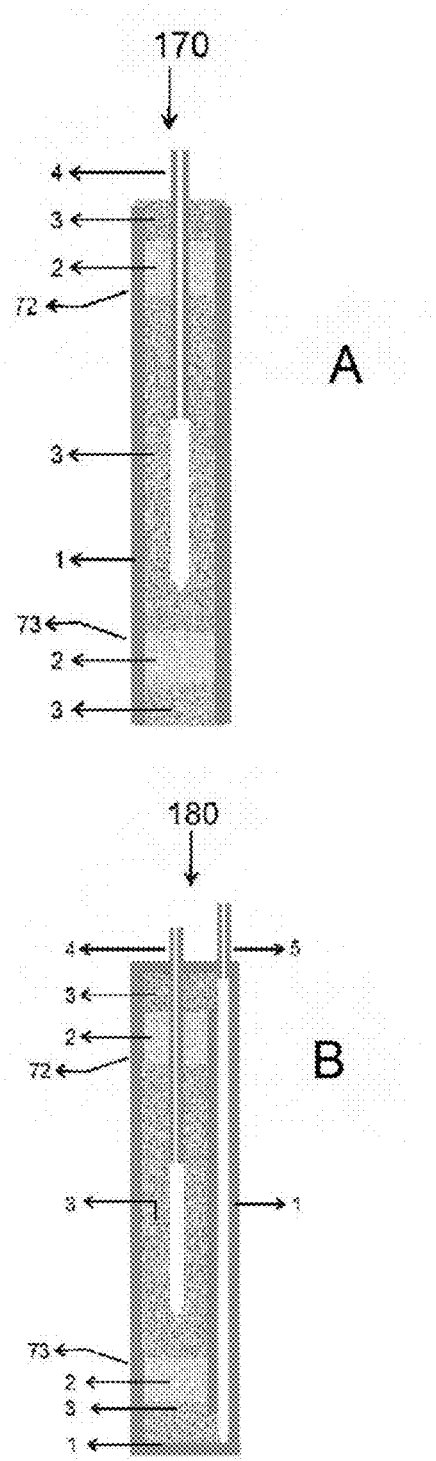
FIG. 15: A—Simple hard sensor (170) for use in systems with purely positive pressurization of dual-depth air, with responsive aggregation through an air inflow duct (4) containing the common porous support element (1), two non-sintered core layers (2), one for the most superficial or upper sensor (72) and the other for the deepest or lower sensor (73), porous blocks (3) open at the ends and porous center-communicating block (3), linked through a common air inflow duct (4).

Extremely simple, these dual sensors (180) provide automation using just one common air inflow duct (4), as illustrated in FIG. 15A. In a slightly more complex arrangement, dual sensors may provide automaton assisted by the internal air flow in the upper sensor (72) and in the lower sensor (73) between the common air inflow duct (4) and the common air outflow duct (5), as illustrated in FIG. 15B.

In the arrangement illustrated in FIG. 15A, the dual sensor (180) is suitable for use with pressurized air under positive pressure, as occurs, for example, in the gas compression irrigation rods of FIGS. 6 and 10. In these systems, the connection is made by way of the air inflow duct (4) of the sensor (6). In the sensor of FIG. 15A, the air outlet, both of the upper sensor (72) and the lower sensor (73), occur through the porous blocks (3), directly into the soil (7), without the risk of suctioning soil particles into the inside of the non-sintered core (2).

The dual soil-water sensor (6) of FIG. 15A has simple responsive aggregation between the lower sensor (73) and the upper sensor (72), which occurs through a common air inflow duct (4), taken through a porous block (3) shared between the non-sintered cores (2) of the upper sensor (72) and of the lower sensor (73). At the ends of the dual sensor, the porous blocks (3) are open for contact with the soil (7). The upper sensor (72) corresponds to the upper non-sintered core (2), whereas the lower sensor (73) corresponds to the lower non-sintered core.

To control the watering throughout the effective depth of the root system, the dual sensor (180) having non-sintered core (2) can be manufactured with different lengths. The technical definition of the length of this sensor can be obtained by different means. It is particularly desirable to consider, for example, the length equivalent to ⅔ of the effective maximum root depth of the plant. In accordance with the details of installation and control of the upper sensor (72) and the lower sensor (73) have an effective sensitivity height that is based on the height of the layer of glass spheres, for example, of the non-sintered core (2). This thickness of the non-sintered core governs the permeability of the sensor to the air in a given soil-water. Where this permeability does not become limiting, then it is desirable that the sensitive range of the sensor at each depth is determined by a thickness of glass spheres between ⅛ to ¼ of the height of the porous support element (1). Regardless of the industrial choice of the thickness of the non-sintered core (2) layer, the construction should preferably use the entire length by technical beginning of the sensitivity, near or at the very ends of the porous support element (1) in relation to the upper (72) and lower (73) sensors.

Using the above specification, irrigation management or control of a plant or crop with a maximum effective root depth of 45 cm can be carried out using a dual sensor (180) measuring 30 cm in length. For vegetables, such as tomatoes, for instance, the dual sensor can be specified with lower (73) and upper (72) sensors with critical tension or bubbling pressure (equation 1) equal to 25 kPa. The sensor is installed in an orifice measuring 45 cm deep produced with an auger.

Therefore, when the water tension in the soil between 15 and 30 cm reaches the critical value, which makes the sensor permeable to the passage of air, the irrigation is activated, for example, by way of an irrigation rod. After watering, when the wetting front reaches between 15 and 20 cm deep, the water moistens the upper sensor (72), which becomes air impermeable, and which may turn the irrigation off, that is, if the lower sensor (73) is also in moist soil. Unlike in dry soil, irrigation would continue until the wetting from reaches the lower sensor (73) and terminates irrigation. A new watering will begin as soon as the water tension in the soil around the upper sensor (72) or the lower sensor (73) becomes greater than the critical tension Pb (eq. 1).

The sensors (170 and 180) of FIGS. 15A and 15B may be constructed with different lengths to meet plant applications with different root depths. In these dual sensors, the most important technical aspects are the thickness and the cross-section of the non-sintered core (2) layer. The adjustment of these parameters is solved considering the passage of water through the porous element (1) and the size of the particles that form the non-sintered core (2). It is important in the dual sensor (6) that the movement of water in the soil, in saturated state, occurs more quickly than along the length of the sensor. This aspect is easily met using porous elements (1) of high critical tension, which can be made of silicon carbide, alumina or mullite with an outer diameter of around 2 cm and an internal diameter of around 1.3 cm with lengths varying between 20 cm and 120 cm.

Sensors with miniature cross-section, around 0.1 cm2, for example, and filled with glass spheres with bubbling pressure of 20 kPa, for example, may activate the irrigation rods as illustrated in FIG. 6. Accordingly, it is suffice to determine a cross-section of non-sintered core that assures the air flow through the sensor of around 200 ml/(h kPa). This technical air flow setting is performed in a laboratory, applying a specific air pressure gradient and by measuring the air flow through the sensor with a bubblemeter. Evidently, this measurement is easier in sensors that have an air inlet tube (4) and air outlet tube (5), as illustrated in the sensors in FIGS. 1 and 15 B.

In cases of sensors having low critical tension, for example 5 kPa, and with sections larger than 1 cm in diameter, the flows are general high (>500 ml/(h kPa) even when the layer (cross-section) of non-sintered core is relatively thick (4 cm). In these applications, depending on the system employed, there may be a need to add air flow restrictions, as illustrated in FIG. 6, or restrictions to limit the water flow, as illustrated in FIGS. 10 to 13.

The dual soil-water sensor (180) of FIG. 15B has aggregate response through the air inflow (4) and outflow (5) ducts. The scheme of this sensor is similar to the sensor illustrated in FIG. 10, which differs by being closed at the two ends, preferably by the very porous element (1) and by containing the air outflow duct (4) linking the porous blocks (3) affixed at the ends. The air outflow duct (5) is ideal for fitting in negative pressure devices such as in the differential valve irrigation rod pressurized by water column illustrated in FIG. 14.

The dual sensors (FIG. 15A and FIG. 15B) can be designated to have equal or different critical water tensions in the soil (Pb, eq. 1) of the upper sensor (72) and of the lower sensor (73). The possibility of building a dual sensor, having two depths, with two different critical tensions is a useful advantage in irrigation management and automatic irrigation control applications. Thus, for example, when using 30 kPa in the upper sensor (72) and 20 kPa in the lower sensor (73) a deepening of the root system could be stimulated.

The invention claimed is:

1. Water tension sensor comprising:
a core enveloped by a porous element, said core limited at its ends by porous blocks connected to an air inflow duct and an air outflow duct, passage of an air flow being established through the porous blocks and through the core,
wherein:
the porous element presents higher bubbling pressure than the core and the porous blocks and is air impermeable when wet;
the core is constituted by hard and compacted particles;
the sensor operates via a pneumatic mechanism and without air dissipation; and
the porous blocks provide intermediate communication of the core with an external environment.

2. Water tension sensor as claimed in claim 1, wherein the core is made of hydrophilic material.

3. Water tension sensor as claimed in claim 2, wherein the hydrophilic material has a cosine of the contact angle greater than 0.9.

4. Water tension sensor as claimed in claim 1, wherein the core is made of material selected from among corundum and glass spheres.

5. Water tension sensor as claimed in claim 1, wherein the porous element is made of hydrophilic material.

6. Water tension sensor as claimed in claim 5, wherein the hydrophilic material has a cosine of the contact angle greater than 0.9.

7. Water tension sensor as claimed in claim 1, wherein the porous element is made of material selected from the group consisting of ceramic, gypsum, and pervious concrete.

8. Water tension sensor as claimed in claim 1, wherein the porous blocks are made of elastic porous materials.

9. Water tension sensor as claimed in claim 1, wherein the porous element has a bubbling pressure four times greater than a critical tension of the core.

10. Water tension sensor as claimed in claim 1, further comprising an adjacent measuring device.

11. Water tension sensor as claimed in claim 10, wherein the measuring device comprises a measuring cavity connected to a measuring duct, the measuring cavity and the core being surrounded by the porous element.

12. System for characterization and continuous readings of water tension, said system comprising:
a water tension sensor,
a cylinder of compressed air,
a shutoff valve,
a restrictor,
a pressure transducer, and
an air duct,
wherein:
the water tension sensor comprises a core enveloped by a porous element, said core limited at its ends by porous blocks connected to an air inflow duct and an air outflow duct;
the porous element presents higher bubbling pressure than the core and the porous blocks and is air impermeable when wet;
the core is constituted by hard and compacted particles;
the shutoff valve, the restrictor and the pressure transducer are directly connected to the air duct; and
the cylinder of compressed air is connected to the air inflow duct of the sensor by way of the air duct, the connection being respectively intermediated by the shutoff valve, the restrictor and the pressure transducer.

13. System as claimed in claim 12, wherein:
the sensor operates via a pneumatic mechanism and without air dissipation, and
passage of an air flow being established through the porous blocks and through the core.

14. System as claimed in claim 13, wherein the core is made of hydrophilic material.

15. System as claimed in claim 14, wherein the hydrophilic material has a cosine of the contact angle greater than 0.9.

16. System as claimed in claim 13, wherein the core is made of material selected from a group consisting of corundum and glass spheres.

17. System as claimed in claim 13, wherein the porous element is made of hydrophilic material.

18. System as claimed in claim 17, wherein the hydrophilic material has a cosine of the contact angle greater than 0.9.

19. System as claimed in claim 13, wherein the porous element is made of material selected from a group consisting of ceramic, gypsum, and pervious concrete.

20. System as claimed in claim 12, wherein the porous blocks are made of elastic porous materials.

21. System as claimed in claim 12, wherein the porous element has a bubbling pressure four times greater than a critical tension of the core.

22. System as claimed in claim 12, further comprising a vacuum pump, a vacuum regulator, and a Richards chamber.

23. System as claimed in claim 22, wherein the vacuum regulator connects to the vacuum pump and to the Richards chamber through, respectively, an intermediary duct and a vacuum duct.

24. System for indicating critical water tension, said system comprising:
   a bubbling display,
   mineral oil,
   a source of compressed air,
   a water tension sensor,
   a flat porous element,
   resin,
   an air inflow duct,
   an air outflow duct,
   a restrictor, and
   a shutoff valve,
   wherein:
      the water tension sensor comprises a core enveloped by a porous element, said core limited at its ends by porous blocks connected to an air inflow duct and an air outflow duct;
      the mineral oil is kept within the bubbling display and the flat porous element, the bubbling display and the flat porous element fastened in dihedral with the resin;
      the water tension sensor is connected through the air outflow duct to an orifice in dihedral;
      the shutoff valve and the restrictor are connected directly to the air inflow duct; and
      the source of compressed air is connected through the air inflow duct to the water tension sensor, the connection being respectively intermediated by the shutoff valve and the restrictor.

25. System as claimed in claim 24, wherein the source of compressed air is at least one of a cylinder of compressed air or an air compressor.

26. System as claimed in claim 25, wherein:
   the porous element presents higher bubbling pressure than the core and the porous blocks and is air impermeable when wet;
   the core is constituted by hard and compacted particles; and
   the sensor operates via a pneumatic mechanism and without air dissipation, passage of an air flow being established through the porous blocks and through the core.

27. System as claimed in claim 26, wherein the core is made of hydrophilic material.

28. System as claimed in claim 27, wherein the hydrophilic material has a cosine of the contact angle greater than 0.9.

29. System as claimed in claim 26, wherein the core is made of material selected from the group consisting of corundum and glass spheres.

30. System as claimed in claim 26, wherein the porous element is made of hydrophilic material.

31. System as claimed in claim 30, wherein the hydrophilic material has a cosine of the contact angle greater than 0.9.

32. System as claimed in claim 26, wherein the porous element is made of material selected from the group consisting of ceramic, gypsum, and pervious concrete.

33. System as claimed in claim 24, wherein the source of compressed air is a rubber bulb.

34. System as claimed in claim 33, wherein the compressed air is generated by manual compression of the rubber bulb.

35. System as claimed in claim 33, wherein the system comprises a reservoir and a unidirectional air valve.

36. System as claimed in claim 35, wherein the reservoir is aimed to define the limitation of maximum pressure and the unidirectional air vale enables repeated manual drive.

37. System as claimed in claim 24, wherein the air coming from the sensor is conveyed to the orifice in dihedral.

38. System as claimed in claim 37, wherein the air coming from the sensor is conveyed through the air outflow duct.

39. System as claimed in claim 24, wherein the porous blocks are made of elastic porous materials.

40. System as claimed in claim 24, wherein the porous element has, at least, a bubbling pressure four times greater than a critical tension of the core.

41. Irrigation rod comprising:
   a water tension sensor,
   an air inflow duct,
   an air outflow duct,
   a chamber,
   a water outflow duct, and
   a waterproof plate,
   wherein:
      the water tension sensor comprises a core enveloped by a porous element, said core limited at its ends by porous blocks connected to an air inflow duct and an air outflow duct;
      the chamber comprises a float, a lid endowed with an air exhaust orifice, and a water inflow duct;
      the air inflow duct and the air outflow duct are in communication with the ends of the water tension sensor, respectively by a sensor air inflow duct and a sensor air outflow duct;
      the water outflow duct communicates directly with the chamber and indirectly with the air outflow duct through a passage;
      the waterproof plate has an interfacing element A and an interfacing element B; and
      the waterproof plate separates the water tension sensor from the other elements of the irrigation rod, allowing communication exclusively through the interfacing elements A and B.

42. Irrigation rod as claimed in claim 41, wherein:
   the porous element presents higher bubbling pressure than the core and the porous blocks and is air impermeable when wet;
   the core is constituted by hard and compacted particles; and
   the sensor operates via a pneumatic mechanism and without air dissipation, passage of an air flow being established through the porous blocks and through the core.

43. Irrigation rod as claimed in claim 42, wherein the core is made of hydrophilic material.

44. Irrigation rod as claimed in claim 43, wherein the hydrophilic material has a cosine of the contact angle greater than 0.9.

45. Irrigation rod as claimed in claim 42, wherein the core is made of material selected from the group consisting of corundum and glass spheres.

46. Irrigation rod as claimed in claim 42, wherein the porous element is made of hydrophilic material.

47. Irrigation rod as claimed in claim 46, wherein the hydrophilic material has a cosine of the contact angle greater than 0.9.

48. Irrigation rod as claimed in claim 42, wherein the porous element is made of material selected from the group consisting of ceramic, gypsum, and pervious concrete.

49. Irrigation rod as claimed in claim 42, wherein the porous element has a bubbling pressure four times greater than a critical tension of the core.

50. Irrigation rod as claimed in claim 41, wherein the chamber contains irrigation water and is refilled by the water inflow duct.

51. Irrigation rod as claimed in claim 41, wherein the air inflow duct communicates with the sensor air inflow duct through the interfacing element A.

52. Irrigation rod as claimed in claim 41, wherein the air outflow duct communicates with the sensor air outflow duct through the interfacing element B.

53. Irrigation rod as claimed in claim 41, wherein the porous blocks are made of elastic porous materials.

\* \* \* \* \*